(12) United States Patent
Battlogg

(10) Patent No.: US 11,266,867 B2
(45) Date of Patent: Mar. 8, 2022

(54) TRAINING EQUIPMENT AND METHOD

(71) Applicant: INVENTUS ENGINEERING GMBH, St. Anton I.M. (AT)

(72) Inventor: Stefan Battlogg, St. Anton I.M. (AT)

(73) Assignee: INVENTUS Engineering GmbH, St. Anton i.M. (AT)

( * ) Notice: Subject to any disclaimer, the term of this patent is extended or adjusted under 35 U.S.C. 154(b) by 65 days.

(21) Appl. No.: 16/090,338

(22) PCT Filed: Mar. 31, 2017

(86) PCT No.: PCT/EP2017/057791
§ 371 (c)(1),
(2) Date: Oct. 1, 2018

(87) PCT Pub. No.: WO2017/168004
PCT Pub. Date: Oct. 5, 2017

(65) Prior Publication Data
US 2019/0111300 A1    Apr. 18, 2019

(30) Foreign Application Priority Data

Mar. 31, 2016    (WO) .................. PCT/EP2016/057162

(51) Int. Cl.
*A63B 21/008*    (2006.01)
*F16F 9/53*    (2006.01)
(Continued)

(52) U.S. Cl.
CPC .......... *A63B 21/00845* (2015.10); *A61B 5/22* (2013.01); *A63B 22/0048* (2013.01);
(Continued)

(58) Field of Classification Search
CPC .......... A63B 21/00845; A63B 24/0087; A63B 2024/0093; A63B 2220/30;
(Continued)

(56) References Cited

U.S. PATENT DOCUMENTS 5,409,435 A    4/1995    Daniels
5,711,746 A *    1/1998    Carlson .............. A63B 21/0056
482/112
(Continued)

FOREIGN PATENT DOCUMENTS

| | | |
|---|---|---|
| DE | 102012017423 A1 | 3/2014 |
| EP | 2408526 A1 | 1/2012 |
| WO | 9733658 A1 | 9/1997 |
| WO | 2006099484 A1 | 9/2006 |
| WO | 2008093938 A1 | 8/2008 |
| WO | 2010108170 A1 | 9/2010 |

*Primary Examiner* — Jennifer Robertson
(74) *Attorney, Agent, or Firm* — Laurence A. Greenberg; Werner H. Stemer; Ralph E. Locher

(57) ABSTRACT

Training equipment is configured for targeted muscle actuation. The training equipment contains a muscle-powered actuating element and a damping system having two components that can move in relation to one another. One of the components is operatively connected to the actuating element, such that a movement of the actuating element can be damped. A field-sensitive rheological medium and a field generation system are associated with the damping system, in order to generate and control the field strength. A damping characteristic can be influenced by the field generation system. A control system is suited and configured to control the field generation system in a targeted manner in accordance with a training parameter, such that the movement of the actuating element can be damped taking into account the training parameter.

29 Claims, 12 Drawing Sheets

(51) Int. Cl.
*A63B 22/00* (2006.01)
*A63B 22/02* (2006.01)
*A63B 22/06* (2006.01)
*A63B 24/00* (2006.01)
*A61B 5/22* (2006.01)
*H04M 1/72409* (2021.01)

(52) U.S. Cl.
CPC .......... *A63B 22/0076* (2013.01); *A63B 22/02* (2013.01); *A63B 22/0605* (2013.01); *A63B 24/0087* (2013.01); *F16F 9/535* (2013.01); *A63B 2024/0093* (2013.01); *A63B 2220/30* (2013.01); *A63B 2220/40* (2013.01); *A63B 2220/51* (2013.01); *A63B 2220/54* (2013.01); *A63B 2220/56* (2013.01); *A63B 2230/06* (2013.01); *H04M 1/72409* (2021.01)

(58) Field of Classification Search
CPC ............ A63B 2220/40; A63B 2220/51; A63B 2220/54; A63B 2220/56; A63B 2230/06; F16F 9/535–537
See application file for complete search history.

(56) References Cited

U.S. PATENT DOCUMENTS

| | | | | |
|---|---|---|---|---|
| 5,816,372 | A | * | 10/1998 | Carlson .............. A63B 21/0056 188/267.2 |
| 5,980,435 | A | * | 11/1999 | Joutras ................ A43B 1/0054 482/114 |
| 9,403,056 | B2 | | 8/2016 | Weinberg et al. |
| 10,054,186 | B2 | | 8/2018 | Battlogg et al. |
| 2007/0010772 | A1 | | 1/2007 | Ryan |
| 2007/0045068 | A1 | | 3/2007 | Namuduri et al. |
| 2009/0017993 | A1 | | 1/2009 | Khanicheh et al. |
| 2010/0035737 | A1 | | 2/2010 | Kwon et al. |
| 2010/0231069 | A1 | * | 9/2010 | Liao .................... H02K 7/1025 310/77 |
| 2011/0112441 | A1 | * | 5/2011 | Burdea .............. G06F 19/3418 600/595 |
| 2011/0275480 | A1 | * | 11/2011 | Champsaur ........ A63B 21/0058 482/4 |
| 2013/0260968 | A1 | | 10/2013 | Shkolnik |

* cited by examiner

TRAINING EQUIPMENT AND METHOD

BACKGROUND OF THE INVENTION

Field of the Invention

The present invention relates to training equipment for targeted muscle actuation with at least one at least partially muscle-powered actuating element and at least one damping system.

A key feature of training equipment is its adaptability to specific training requirements and to the individual needs of the training user. Therefore, training equipment usually has different possible settings. For example, it is possible to set which force the training user must apply or how much they must stretch or extend.

However, setting training equipment is often very uncomfortable and time-consuming. Specialized knowledge is usually required in order to be able to optimally make the settings necessary for targeted training. Overloading and pain may even arise due to incorrect settings.

In the prior art, therefore, training equipment is known in which the training movements are influenced by dampers. This usually makes it easier to set specific training requirements.

For optimal training and a particularly comfortable use of training equipment, however, it would be advantageous if the setting of the corresponding damper could be even more targeted and in particular also at least partially automated.

SUMMARY OF THE INVENTION

It is therefore an objective of the present invention to provide training equipment and a method for operating training equipment, which allow improved training and in which targeted settings may be made particularly inexpensively and preferably in addition, in an at least partially automated way.

This objective is achieved by training equipment having the features of the main apparatus claim and a method having the features of the main method claim. Preferred developments of the invention are the subject matter of the dependent claims. Further advantages and features of the present invention will become apparent from the general description and the description of the exemplary embodiments.

The training equipment according to the invention is used for targeted muscle actuation and comprises at least one at least partially muscle-powered actuating element. The training equipment comprises at least one damping system with at least two components that are movable relative to one another. One of the components is operatively connected to the actuating element, so that a movement of the actuating element may be damped. The damping system is associated with a field-sensitive rheological medium and at least one field generation system for generating and controlling a field strength. At least one damping characteristic may be influenced by the field generation system.

In a preferred development, the training equipment comprises at least one control system. The control system is particularly suitable and designed for targetedly controlling the field generation system based on at least one training parameter. Preferably, in this way, the movement of the actuating element may be damped based on the training parameter.

The training equipment according to the invention affords many advantages. By means of the corresponding damping system of the training equipment, the training may be significantly improved, because the damping may be adjusted in a highly targeted way. In addition, the desired settings for the training may be made particularly comfortably and inexpensively.

The control system is also particularly advantageous. By means of this system, the field generation system may be set in such a way that training with highly targeted training parameters is possible. In addition, an automated setting of the training equipment may take place via the control system. For this purpose, a trainer or therapist may determine the required training parameters in advance, and store them in the training equipment. Or the user may receive the training parameters online or from the Internet. The training user may then start training without having to change any settings themselves or wait for the trainer.

In particular, the training parameter is stored in the control system. The training parameter may also be stored on a storage medium that is operatively connected to the control system. For example, the training parameter may be stored on a portable storage medium that the training user brings along. In this case, by insertion of the storage medium or also by a near field detection, an automated setting of the desired training parameters may take place when the training user uses the training equipment.

In particular, a damping force to be applied for moving one of the two components may be set based on the training parameter. The actuating force of the actuating element may be adjusted, in particular, by means of the damping force.

Preferably, a path and/or a rotation angle may be set based on the training parameter, and at least one of the two components may be moved via this path or angle. In this way, in particular the path and/or angle of rotation of the movement of the actuating element may be adjusted. It is also possible that the mobility of the actuating element may be limited and/or blocked by adjusting the damping force. In this way, for example, a movement of the actuating lever outside a predetermined path or angle of rotation may be prevented. The blocking of the actuating element takes place in particular by setting a correspondingly high damping force, so that, for example, the actuating element is no longer movable by muscle power.

Preferably, the damping characteristic is variable at least during a single actuation of the actuating element. In particular, a single actuation of the actuating element may be carried out with different damping characteristics and, for example, with different damping forces. In particular, the damping characteristic may be varied during a single movement cycle. The movement cycle may, for example, be a single turn with the right and/or left leg.

For example, the actuation is a pull on an arm lever or a pivoting of a leg lever. Then, damping characteristics, and preferably damping forces, may be adjustable at the beginning of the pulling or pivoting that are different than those during the further progression or toward the end of the pulling or pivoting.

The adjustment of the damping characteristic during an actuation may be described by at least one function. The function is preferably stored in the control system.

This offers considerable advantages over a damping that remains at a specific value throughout the actuation. In many exercises, it is of great advantage if just at the beginning or near the end of the respective movement or actuation, the damping force is lowered or raised in a targeted fashion. Due to the damping system with the rheological medium or with the field generation system, the damping force may be varied almost arbitrarily during a single actuation by adapting the field strength. This offers significant advantages over training equipment that must be adjusted via mechanical valves.

This makes it possible for the training process during the training period to proceed in a particularly individual and targeted fashion. This offers considerable advantages over adaptations that take place over a longer duration and e.g. for the warm-up phase, main training phase, or cool-down phase, which each respectively may be e.g. several minutes or hours long. This is because while the body parts to be trained are usually loaded or acted upon synchronously. However, for optimal training in terms of joint protection or best possible muscle building, it is advantageous if the training course is not made roughly variable over a longer period of time, e.g. minutes or even hours, but each movement cycle is determined individually and even differently for the body part to be trained.

The invention presented here, in contrast, offers a very quick adaptation of the settings, for example in real time and/or during a single movement. In one configuration, as a home trainer in the form of a bicycle, for example during a pedal rotation through 360°, the braking force and the torque may be varied in a manner that is controlled by the damper settings. In particularly preferred configurations, the left leg may even be trained differently than the right leg or may be subjected to braking torque and vice versa.

The training parameter is particularly preferably taken from a group of parameters comprising a force or torque, speed or angular velocity, acceleration, distance, direction of movement or direction of rotation, or movement path, furnished for actuation of the actuating element; and an angle furnished for actuating the actuating element. Reflecting such training parameters in the control of the damping system allows a particularly targeted adaptation to the individual training requirements of a training user. The angle may for example specify the range by which the actuating element may be pivoted at a particular force and/or speed.

It is also possible that the training parameter describes at least one parameter of the group as a function of at least one other parameter of the group. For example, the speed and/or the force may be stored in the control system as a function of the distance and/or the angle.

It may be provided that a characteristic value for the training parameter may be input, from which the training parameter may be derived and/or derived indirectly. For example, the trainer may select and enter a value from a training condition scale. A high value is then, for example, for a strong, trained person and a low value is for an untrained person. The control system may then convert the characteristic value into a training parameter that is suitable for controlling the damping system.

The control system is preferably suitable and designed to control the field generation system based on at least one training parameter as a function of at least one other training parameter.

For example, the trainer may assign specific forces for actuating the actuating element to specific angular positions of the actuating element. The control system then takes into account in particular the force as a function of the angle. This has the advantage that a higher or a lower force is required of the training user in specific positions of the actuating element. This is particularly advantageous in rehab exercises, because high forces must be avoided in specific strain positions. Thus, in the rehabilitation of a knee injury, a lower damping and thus a lower actuating force may be furnished with increasing flexion angle of the knee.

In an advantageous configuration, the control system is suitable and designed to detect at least one characteristic for the movement of the actuating element by means of at least one sensor device. In particular, the control system is suitable and designed to targetedly control the field generation system while taking into account the characteristic. In particular, the damping force for the movement of at least one of the two components may be adjusted in view of the characteristic. In particular, the detected characteristic relates to one or more of the magnitudes which are also used as training parameters. In particular, the characteristic describes a force or torque, air pressure, pressure in liquids, speed, acceleration, distance, direction of movement or direction of rotation, movement path and/or an angle, furnished for actuating the actuating element.

Such a configuration has the particular advantage that the adjustment of the damping force not only takes place based on a previously defined training parameter, but is also customizable and particularly preferably also controllable by means of sensor monitoring of the training. So e.g. incorrectly executed exercises and, for example, too-fast movements may be detected without the trainer's presence.

For example, upon detecting too-fast movements, the damping force may be controlled so that the training user performs the exercise correspondingly slower due to an increased damping force.

Preferably, it is also possible that the detected characteristic is stored in the control system. As a result, the trainer has the opportunity to analyze the course of the training retrospectively and possibly adapt the training accordingly.

The control system is preferably suitable and designed to adapt the training parameter based on this characteristic. This enables an intelligent or adaptive adaptation of the training parameter. It is particularly advantageous that the adaptation of the training parameter is done by the control system. This saves the trainer a time-consuming and tedious redetermination of the training parameter. It is also particularly advantageous in such a configuration that the trainer may first specify an empirical value or an approximate value as the training parameter. If this training parameter requires optimization, the control system detects this, in particular on the basis of the sensor-recorded characteristic, and e.g. independently adapts the training parameter.

For example, the sensor-detected characteristic indicates the speed at actuation of the actuating element. If the speed exceeds a threshold value, it may be assumed that the exercise is rather simple. The control system is preferably suitable and designed to adapt the training parameter when a threshold value is exceeded. For example, the control system sets the force required for actuation to a higher value based on the damping force. This automatically keeps the training level at an advantageous level.

The control system is particularly preferably suitable and designed to carry out a durable adaptation of the training parameter. As a result, the adapted training parameter, and not the original training parameter, may also be used in later training units. It is also possible that there is only a temporary adaptation of the training parameters by the control system. For example, the training parameter is adapted only for one session or actuation.

In all configurations, it is particularly preferred that the damping system is suitable and designed to adjust the damping characteristic in real time. In particular, the damping system is suitable and designed to adjust the damping characteristic in real time, taking into account the characteristic. As a result, optimal adaptation to the individual needs of the training user is possible even with fast or very dynamic training procedures.

For example, the actual condition of the training user is detected in real time and the training scope in this form is also adapted in real time by changing the parameters during a training movement. This is preferably adapted for each body part, i.e., the right arm is for example trained differently than the left arm. This is achieved in particular by the fact that the sensor device detects states, in particular by means of different sensors; forwards this data to control electronics; evaluates the data with an algorithm; and outputs the data to fast actuators, which convert it into force or torque. Fast is e.g. a hundred times per second or in less than 100 ms.

A significant advantage of training equipment according to the invention is that the damping system is equipped with a magnetorheological fluid as the working fluid. The magnetic field of the electric coil may be set in real time, i.e. in a few milliseconds (less than 10 or 20 ms), controlled by the control system. In this way, the damping force may be adjusted in real time.

In particular, the damping system is suitable and designed to change the damping characteristic by at least 30% within less than 100 milliseconds. In particular, the damping characteristic may be varied by at least 10%, preferably by at least 30% and particularly preferably by at least 50%, within less than 10 milliseconds. The damping characteristic may also be variable by at least 100% or 500% or by ten or a thousand times, within less than 100 milliseconds. This kind of real-time control is particularly advantageous for training procedures.

Particularly preferably, the damping characteristic may be varied adaptively during a single actuation of the actuating element, taking into account the characteristic. Thus, a wrongly executed and, for example, too-fast actuation of the actuating element may be counteracted particularly quickly by adapting the damping characteristic. This is particularly advantageous in rehabilitation training, as even a single movement that is too vigorous or too extended may cause great pain to the training user. Thus, for example, excessively vigorous movement may be detected at the outset by means of sensors and be prevented by greatly reducing or entirely removing the damping force.

It is possible and preferred that the damping system is suitable and designed to block a muscle-powered movement of the actuating element, by means of the field generation system and the field-sensitive rheological medium.

By this means, specific movements of the training user may be prevented in a targeted fashion. For example, in this way a range of motion may be adapted and/or an overly extensive movement may be stopped. Preferably, the damping system is designed in such a way that the maximum damping force is a multiple of the anticipated muscular force.

Particularly preferably, the movement may be blocked based on the training parameter and/or the characteristic. By this means, disadvantageous training movements may be targetedly and advantageously prevented. Because such blocking may take place particularly quickly and preferably in real time, disadvantageous movements are already prevented at the outset. For example, the trainer may specify an angle or an angular range in which the mobility of the actuating element is targetedly blocked. By means of blockage based on the detected parameter, a disadvantageous movement may be prevented particularly quickly and preferably in real time if the characteristic indicates such a movement.

In all configurations it is preferred that the actuating element is taken from a group of actuating elements, comprising: Pedal drive, leg lever, knee lever, arm lever, back lever, belly lever, trunk lever, cable, oar lever. The actuating element may also be designed as a finger lever and/or hand lever and/or wrist lever. The pedal drive may be formed as a tread plate or may at least comprise such a plate. Preferably, an actuating element is furnished respectively for each finger and/or each foot.

The term "lever" also includes in particular a rocker or a pivotable and/or rotatable lever element, or also a pressure lever or pull lever. In particular, a pulling and/or pressing takes place via the actuating element.

The training equipment may also be designed as a handtrainer or at least may comprise a hand-trainer. In particular, two actuating elements are furnished, which are connected to one another at their end portions via a pivot bearing device. Preferably, the first actuating element is connected with the first component of the damping system and the second actuating element with the second component, and e.g. the rotational damper, so that a pivoting of the two actuating elements may be damped.

The training equipment may also be designed as, or at least comprise, a finger trainer. In this case, an actuating element is respectively furnished for each finger, having at least one damper. The training parameter in this case specifies, among other things, the number of fingers to be moved and/or the type of finger. The dampers of these fingers may then be actuated with a defined damping force, or with a damping curve defined by a function. The dampers of the other fingers are then particularly blocked. All fingers may also be released. Individual damping forces or damping curves may be furnished for each finger.

In an advantageous configuration, the training equipment comprises at least one damping system with at least one rotational damper. In particular, the first component comprises an inner component and the second component comprises an outer component. In particular, the outer component preferably radially surrounds the inner component at least partially. In particular, a damping gap is arranged between the components which is ring-shaped, circumferential, bounded radially inwardly by the inner component and bounded radially outwardly by the outer component and at least partially filled with the rheological medium. The damping gap may be exposed to a magnetic field, in particular by the field generation system, in order to damp a pivoting movement of the two mutually pivotable components about an axis.

Particularly preferably, a plurality of at least partially radially extending arms is furnished on at least one of the components. In particular, at least a part of the arms is equipped with an electric coil with at least one winding. In particular, the winding extends respectively adjacent to the axis and spaced apart from the axis.

A rotational damper of this kind is particularly well suited for use in the training equipment, because it requires little space and may be adjusted very quickly.

In particular, the training equipment comprises at least one transmission device. The transmission device is preferably suitable and designed to at least partially implement a linear movement of the actuating element in a pivoting movement of one of the two components, so that the linear movement may be damped by the rotational damper.

It is also possible that the actuating element itself may be rotatable. Then, the rotational movement of the actuating element preferably may be damped directly by the rotational damper.

Preferably, the training equipment comprises a rotational damper with at least one displacement device, wherein the displacement device has a damper shaft and intermeshing displacement components, and wherein a rotational movement of the damper shaft may be damped. In this case, the displacement device preferably contains at least one magnetorheological fluid as a working fluid and may be operated by that means. A control system is preferably associated, with which a magnetic field from a magnetic field source or magnetic field generation system comprising at least one electric coil may be controlled. The magnetorheological fluid may be influenced by the magnetic field in order to adjust a damping of the rotational movement of the damper shaft.

Preferably, the training equipment comprises a damping system with at least one damper unit, wherein a damping of the rotational movement between the at least two components may be adjusted. In this case, at least one channel is furnished wherein the channel contains a magnetorheological medium. At least one magnetic field generation system is furnished for generating at least one magnetic field in the channel in order to influence the magnetorheological medium in the channel by means of the magnetic field. At least one rotating body is preferably furnished in the channel.

In a development, a free distance between the rotating body and the component is at least ten times as large as a typical average diameter of the magnetically polarizable particles in the magnetorheological medium.

Preferably, at least one acute-angled area containing the magnetorheological medium is furnished between the rotating body and at least one component, and this area may be acted upon by the magnetic field of the magnetic field generation system to selectively link the particles and/or block or release the rotating body.

In this case, the acute-angled area between the rotating body and a component may taper in the direction of the relative movement of the component relative to the rotating body.

In an advantageous development, the damping system comprises at least one linear damper with at least one first damper chamber and at least one second damper chamber. The first and second damper chambers are in particular coupled to one another via at least one controllable damping valve. The damping valve is preferably associated with the field generation system. The field generation system is used in particular to generate and control a field strength in at least one damping channel of the damping valve. The field-sensitive rheological medium is preferably furnished in the damping channel.

A linear damper of this kind may be used particularly well for damping translational or linear movements of the actuating element. It is also possible that the linear damper is operatively connected with the actuating element via at least one transmission device. In this case, the transmission device is particularly suitable and designed to convert a rotational movement of the actuating element at least partially into a translational movement of one of the two components.

In particular, the linear damper comprises a chamber filled with the rheological medium and a piston that is movable relative to the chamber. The piston is in particular operatively connected to the actuating element.

In further preferred configurations, the training equipment or fitness equipment is equipped with at least one rotational damper. In particular, in the context of the present invention, the term "training equipment" also encompasses fitness equipment, and vice versa. The training equipment is suitable and designed for controlled muscle actuation. The equipment comprises at least one at least partially muscle-powered actuating element. At least one movement of the actuating element may be damped by the rotational damper.

In a possible variant, a customer comes e.g. to the fitness center and goes to a body scanner and/or analyzer. Here, the "leverage ratios" are determined and stored (e.g. upper arm, forearm, thighs, height . . . ). The customer receives a device (e.g. a NFC bracelet, chip, smart device such as a smartphone or watch, or the like) which transmits this data to the fitness equipment when the equipment is in use. In this way, the equipment is always optimally adjusted with respect to the training (e.g. force over path, torque over angle or the like) or tells the user how to adjust it (e.g. mechanically adjust the seat or the like) or adjusts the equipment on its own (e.g. by means of electric motors or the like).

In another possible variant, the customer has the data with them (e.g. by means of a smart watch, smartphone, chip or the like). In this case the customer may go to any gym (worldwide) that is able to use this data or has the right fitness equipment (user engagement).

In both variants or a further variant, the data is transmitted again from the fitness equipment to a "memory" (e.g. cloud, internal memory or the like) and evaluated. The customer may then process the data, for example, at home.

The useful profile is preferably refined based on the data (for example, an adaptive configuration may be furnished). The data may also be compared and optimized with colleagues (e.g. via community, cloud or the like). Preferably, a log file is created which displays the training process and outcome. The data may also be sent to diagnosticians, doctors, caregivers or health insurance providers to let them know how and what has been done.

Preferably, at least one control system is furnished and is suitable and designed to adjust the damper in a targeted fashion, taking into account at least one predetermined parameter. The adjustment preferably takes place in real time. For example, a force desired for a muscle exercise may be furnished as a parameter. The damper is then adjusted so that the user must apply the force to move the actuating element.

Preferably, the control system is suitable and designed to register at least one characteristic of the movement of the actuating element. In particular, the control system is suitable and designed to targetedly adjust the damping of the rotational damper in terms of its damping, based on the characteristic.

The characteristic of the movement of the actuating element is detected in particular by at least one sensor. In particular, the detection is continuous. For example, the detection may occur by means of one of the sensors described here and preferably by means of the rotary encoder. The parameter then preferably relates to a threshold value and/or a comparison function for the characteristic. An assignment of a predetermined parameter and detected characteristic may be done in the manner of a mapping.

For example, the caregiver may specify a value for a force/torque desired during the exercise as a parameter. The force/torque applied by the user is then detected as a characteristic of the movement of the actuating element, and is compared with the predetermined value. If the user exceeds this value, the damper may be made softer or more easily movable. In this way, overloading the muscle during training is effectively avoided. This is particularly advantageous for rehabilitation measures, where it is crucial to avoid overloading. Alternatively, the damper may output haptic feedback to the user. With a registered overload, the damper may also be switched to no or very low power.

Preferably, the characteristic describes an angular position and/or a movement direction and/or a torque and/or an acceleration of the actuating element. These characteristics are particularly advantageous because they are characteristic of the user's muscle actuation on the training equipment.

Particularly preferably, the adjustment of the damper takes place as a function of the characteristic. In particular, the adjustment of the damper is dynamic and/or adaptive. This has the advantage that a much more individualized training is possible than with weights or a conventional linear damper setting. For example, a training movement may start out with light force and become heavier with increasing stroke and/or angle of rotation. The force to be applied may also be adjusted in real time based on an acceleration registered as a characteristic. It is also possible to distinguish between the left and right halves of the body and make corresponding adaptations.

In many people, the halves of the body are often trained differently from the outset (e.g. left- or right-handed); the training equipment may particularly preferably be adapted or adjusted to this. This applies particularly after illness or accidents, in which one part of the body is typically more affected than the other (rehabilitation).

The training program may also be varied several times and individually within the training period.

For example, the characteristic describes the angle of rotation during knee extension. In this case, the damper and thus the applied muscle power may be adjusted based on the angle of rotation. For example, the force is reduced with increasing extension of the knee. This prevents harmful training loads. At a critical angle of rotation, the damper may also be adjusted to zero force, so that harmful overextension may be prevented.

Critical angles or positions may also be predetermined by injury or may have a physiological origin. Here, the damper may be preset exactly to these conditions (personalized training).

Because exercises are often carried out too hastily and too fast, which puts addition or even more harmful strain on the joints and musculature, the damper may be adjusted in such a situation, or may automatically adjust itself, so that a fast procedure/movement is not possible or is not allowed. The damper may then be adjusted to become very soft or to send a haptic feedback.

It is also possible that the characteristic describes the direction of movement. As a result, e.g. a different force may be set for a knee stretching than for backward movement or squatting. In many muscle exercises, it is often very important that the return movement is easier or alternatively more power-consuming than the forward movement.

A haptic feedback may also be given to the user during the training. This is done in particular by means of a targeted change in the damping characteristics and preferably as described above. The feedback is output in particular depending on the characteristic of the movement. For example, haptic chatter or jerking may be adjusted by the damper if the characteristic indicates that the user is performing an exercise too quickly or too strongly. The feedback may also be output if the user goes beyond a rotation angle or movement distance, or does not perform an exercise correctly within a movement distance. This allows the user to easily and simply learn how to perform the exercises correctly.

It is also possible that the feedback is output taking into account other sensor values that serve as characteristics. For example, the control system may register pulse values, heart rate and other vital parameters and use these to adjust the damper. If the user overexerts (fatigue condition) or exceeds an appropriate training range, the user will be notified by the haptic feedback and/or the damper will adapt automatically and adaptively in such a way that the user will return to working in an appropriate and preferably non-harmful training range.

It is also possible to adapt the damper properties based on other sensor values and, for example, the vital parameters as a characteristic. Thus, the force to be applied may be increased when the pulse indicates a warmed-up muscle apparatus. It is also possible that the damper in specific angles of rotation is set in such a way that the user may not bring the actuating element into these angles until a specific value of the vital parameters or other characteristics has been registered. This avoids overextending the muscles at the start of the training.

The rotational damper according to the invention may be used in fitness equipment in preferred developments as a damper and in particular as a hybrid damper for existing systems. In this case, for example, in training equipment and for example a fitness bicycle (e.g. Ergotrainer or similar), the rotational damper that is switched in the millisecond range and without intermediate steps may be switched parallel to an existing relatively slow brake (e.g. friction brake, eddy current brake or other suitable brakes). In consequence, it is possible to compensate for load peaks (which, for example, result from kinematic conditions), irregularities, vibrations, wear, bearing clearance and other issues. This is advantageously done as a controlled system.

Hereinafter, by "single actuation" is meant, for example, a pedal rotation in a training bicycle, a partial or complete oar movement (e.g. extension, pull, return or the like) in a rowing machine, opening and closing of a door, etc. It may also refer to a movement of the actuating element of the training equipment.

The rotational damper according to the invention may also be used as the sole energy conversion element (for example a brake or the like), as a result of which hitherto impossible or highly individualized force/torque progressions become possible. For example, the actuating force/torque may be varied not only from one single actuation to another (not just, e.g., per full revolution, per full stroke), but also during a single actuation. In particular, the force/torque may be changed over a path/angle, resulting in a torque that changes multiple times during one revolution and thus a targeted torque curve/characteristic during a revolution.

In a rowing machine, for example, during a complete oar movement, the exact torque progression (e.g., the progression of force on the hand) is generated that would be adequate for a rowing motion in a boat in the water. The rotational damper according to the invention preferably simulates the oar kinematics or actuating kinematics, immersion depth, travel speed, angle of attack of the paddle and many other force progressions of the sport.

In a cross-country skiing or biathlon training equipment, for example, during a complete movement of the arms or the body, an exact force progression may be generated (e.g. progression of force on the hand or the arms and shoulders) that would be adequate for movement on snow. The training equipment according to the invention, with its controllable damping system, preferably simulates the kinematics of actuation, depth of immersion into the snow (particularly adjustable so that different types and types of snow may be simulated), adjustment of the angle of attack in the snow, travel/operating speed, angle of attack of the pole to the body, angle and positions that arise when going up or down and many other force progressions of the sport. In this case, linear and/or rotational dampers may be used, which may also be combined with adjustable springs (spring stiffness, spring travel). Preferably, the damping system is associated with at least one spring device.

Depending on the configuration of the training equipment, both the damping and also the spring force may be adjusted. Thus, the working range of the training equipment, but in particular the training equipment itself, may be better tailored to the user. Adjustment relative to the user's weight or condition on the day is usually useful. When using e.g. coil springs, this adjustment may be done by manually or automatically adjusting (e.g. with an electric motor) the spring support surface. This changes the spring length (linear length) in particular. In torsion springs, the spring bar end may have a toothing which engages with a housing. Other torques may be generated by rotating the basic position. Preferably, any suitable spring types may be used (spiral spring, torsion spring, coil spring, spiral spring, leg spring, bar spring, coil spring, gas-pressure spring).

A comfortable way of making adjustments is e.g. by means of an air spring or gas spring. The air spring is a spring system that exploits the compressibility of gases, particularly air. In this case, the air (ambient air), for example, is enclosed in a rolling lobe air spring, which is connected airtightly with other parts such as the cover and rolling piston. The rolling lobe air spring is slipped over the piston in particular and unrolls in particular when there is pressure on the piston. The air spring may be supplied with compressed air by a hand pump (e.g. bicycle pump) and/or a compressor. Depending on the desired training range, body weight or loading (dead weight of the parts of the training equipment), air may be pumped in or out to increase or decrease the spring force. Via the filling volume, the level position (longitudinal extent) may also be held constant and/or varied. The air spring is also particularly advantageous in training equipment because it is particularly clean and easy to adjust or set.

Dynamically adapting the spring force, similar to the dynamic damping adjustment, in particular increases the functional range of the training equipment. Preferably, the spring device or the spring force is adjustable analogously to the above-described damping system or damping force.

In particular, for a left half of the body, an at least partially different damping characteristic may be set than for a right half of the body. Preferably, another different damping force to be applied may be set for the left half of the body than for the right half of the body.

In particular, at least one actuating element BE is furnished for each half of the body. For example, at least one actuating element is provided for each leg and/or arm and/or hand and/or half of the trunk. In this case, the respective actuating elements may include a separate damper. In this case, each damper is preferably individually adjustable. For example, the damping for the right arm or the right leg may be set differently than for the left arm and the left leg, respectively.

The respective actuating elements may also be damped together or may comprise at least one shared damper. For example, the actuating elements are designed as cranks, which are operatively connected via a shared shaft. In this case, each crank may respectively represent an actuating element, wherein the rotational movement of the shared shaft is damped. Preferably, a damper setting may be adjusted when the left leg presses down on the left crank and the right leg is carried along, which is different from the one adjusted when the right leg presses down on the right crank and the left leg is carried along. In particular, a different damping may be adjusted depending on the angular position of the actuating element for the respective half of the body. In particular, the damper setting may be set depending on which half of the body or with which actuating element the greater or lesser force is applied to the damper.

A cooperation of the two halves of the body or actuating elements may be taken into account, so that the degree of difference between the halves of the body settings may be adapted dynamically. For example, in setting the damper for the left arm, the force progression or angle of rotation of the right arm is detected by sensors and taken into account. If differences are recognized between the halves of the body or actuating elements, the damper setting may be adapted individually for each half of the body. For example, if the right arm suffers from disease and fatigues faster, the damping force for the left arm may also be adapted to prevent an unhealthy imbalance. But on the other hand, an imbalance may be set which is advantageous for training.

The damping characteristic also may be set differently for a combination of body parts of one half of the body and/or different halves of the body. For example, an arm-leg combination may be made crosswise or on one half of the body. For example, it is possible to have a different damper setting for a left leg and a right arm than for a right leg and a left arm.

Preferably, the damping characteristic furnished for a particular half of the body may be varied at least partially during a single actuation of the actuating element. Preferably, for the half of the body to be influenced or selected, the damping force may be varied during a single movement cycle and in particular may be changed multiple times.

Arms and legs and many muscles are usually present on the left and right. For most people, these are developed or trained to very different degrees. In addition, flexibility differs greatly from person to person or even from the left to the right half of the body. This particularly occurs after an accident or after injuries. Even the most modern training or rehabilitation equipment usually does not consider this. Therefore, the invention offers particular advantages in this respect, because the halves of the body may be addressed differently in a targeted fashion, e.g. even during a single movement.

In particular, the damping characteristic is may be varied at least partially based on at least one signal from a near field detection system. The damping characteristic may also be varied based on at least one preferably intelligent evaluation of the signal of the near field detection system. In particular, the damping force may be varied based on the signals and the subsequent intelligent evaluation of a near field detection system.

The near field detection system comprises in particular at least one near field sensor. For example, the following may be furnished: optical sensors, surround view camera, ultrasound, image recognition, laser. For this purpose, existing sensors (e.g. Microsoft Kinetics) and/or sensors coupled to a smartphone may also be combined with the training equipment. The near field detection system is particularly suitable and designed to create and/or at least partially adapt the training parameter, in particular based on the detected signal.

The near field detection system recognizes e.g. the posture. The control system reduces e.g. the forces when for example the back is greatly bent, in order to train the lifting of a weight. A bent back usually leads to a high disc load and thus to possible health damage. Therefore, it is preferable to increase the force as soon as or when the back curvature ceases, so that a good training result is achieved. Continuous monitoring of the training with adaptations for targeted improvement may be carried out in this way. This is particularly true not only for sports studios or professional equipment, but also for home use.

The method according to the invention serves to operate training equipment for targeted muscle actuation. An at least partially muscle-powered actuating element is actuated. The training equipment comprises at least one damping system with at least two components that are movable relative to one another. One of the components is operatively connected to the actuating element, so that a movement of the actuating element may be damped. The damping system is associated with a field-sensitive rheological medium and at least one field generation system for generating and controlling a field strength. The field generation system influences at least one damping characteristic. In this case, the field generation system is controlled in a targeted fashion, based on at least one training parameter with at least one control system, so that the movement of the actuating element is damped taking into account the training parameter.

Preferably, the above-described training equipment according to the invention is operated according to the method of the invention.

The method of the invention provides an inexpensive and at the same time highly individualized adaptation of settings for training.

In particular, at least one characteristic is monitored for at least a single actuation of the actuating element. The damping characteristic is preferably set in a targeted fashion, taking into account the characteristic, so that a force/torque profile may be set that is optimal with regard to the desired training result. Preferably, this is monitored and/or adjusted in real time. In particular, taking into account the training parameter, a single movement of the actuating element during a single actuation is preferably monitored in real time and influenced or damped and controlled in a targeted fashion by an actuator, in such a way that an optimal force/torque curve results with regard to the desired training result. In particular, at least the above-described sensor device is furnished for this purpose.

In particular, the setting of the damping characteristic is done more than once, preferably several times, taking the characteristic into account, during a single actuation of the actuating element. In this case, the actuation is e.g. one revolution of the actuating element. The adjustment may also be made continuously during a single actuation. Preferably, the detection of the characteristic also takes place repeatedly and/or continuously during a single actuation.

In particular, less than 100 ms elapse between the actuation of the actuating element, for which the characteristic is monitored, and the resulting adjustment of the damping characteristic. Less than 10 ms is also possible. The adjustment takes place in particular in real time and preferably in the manner described above for the training equipment.

In particular, at least one characteristic value is determined in real time for a relative movement of the first and second components relative to each other, and in particular is repeated and e.g. determined periodically. In particular, a field is only generated with the field generation system if there is a movement of the first and second components relative to each other. In particular, by means of the characteristic value, a field strength to be set is derived, in particular in real time. In particular, by means of the field generation system, preferably in real time, the field strength to be set is generated in order to adjust in real time a damping characteristic, in particular a damping force, that is derived from the determined characteristic value. In particular, less than 100 ms, preferably less than 10 ms, elapse between the relative movement and the resulting adjustment of the damping characteristic. In particular, less than 100 ms, preferably less than 10 ms, elapse between the determination of the characteristic value and of the damping characteristic derived therefrom. The adjustment of the damping characteristic takes place in particular more than once and preferably several times during an actuation of the actuating element.

The training equipment may comprise at least one active or passive cooling device.

The damping system of the training equipment may in particular be designed in the manner described for damping systems in DE 10 2012 016 948 A1 and WO 2017/013234 A1 as well as WO 2017/013236 A1. The subject matter of these documents and in particular the construction principles of the dampers described therein are therefore fully incorporated by reference into the specification of the present invention.

Further advantages and features of the present invention will become apparent from the description of the exemplary embodiments, which are explained below with reference to the accompanying drawings.

DESCRIPTION OF THE INVENTION

Figure 1:
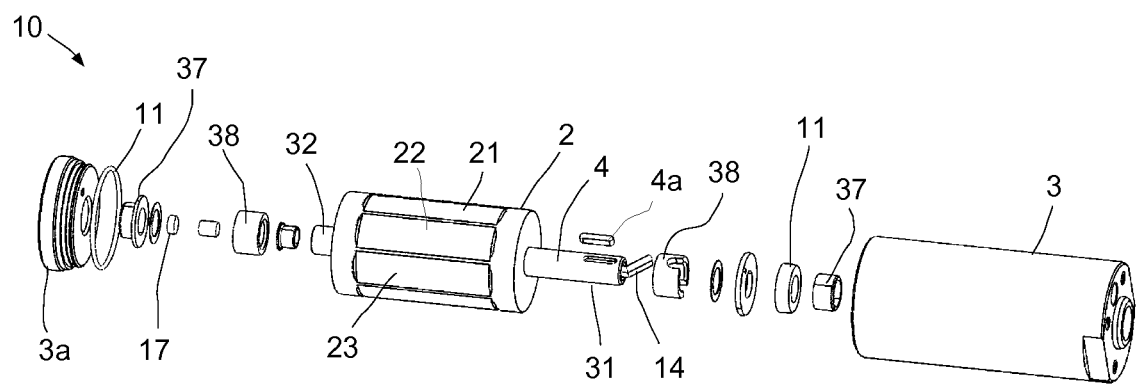
FIG. 1 a schematic exploded view of a rotational damper according to the invention.

FIGS. 1 to 18 show different training equipment 300 or fitness equipment. Without limitation, the fitness equipment may be used as a device for building muscle, for example, as a leg press, as a weight bench, as a cable pulling station, as a traction unit, as a multi-press rack, as a stepper and as a strength training station.

It may also be used on weights. The invention may also be used in fitness equipment for endurance enhancement, such as ergometers and crosstrainers, treadmills and rowing machines.

The invention affords advantages, e.g. when configured as a leg press, because in that case large weights might be used in combination with too weak muscles and the stretching of the legs may lead to a buckling of the legs backwards and thus to serious injuries. This may be avoided by means of the invention. Training equipment according to the invention having an (adaptive) damping system may prevent this in a targeted fashion, by a position detection taking place or by the force being generated based on the angle. Only (a correspondingly adapted) force is preferably applied, even when pressed.

The same is true when lifting a weight. In this case also, the body position may be disadvantageous, e.g. when lifting (picking up) the weights, the back is more curved, which generates high loads on the vertebrae. Fitness equipment with a controllable (adaptive) damping system may be optimally adapted here.

A possible use in a Variant A may be as follows:

The customer comes into the fitness center and goes to a body scanner. Here, the "leverage ratios" are determined and stored (upper arm, forearm, thighs, height . . . ). The customer receives a device (computer, bracelet, chip, smartphone or smartwatch, or the like) which transmits this data to the equipment while using the equipment. Thus, the equipment is always set optimally, or tells the customer how to adjust (for example, mechanically adjust seat . . . ), or adjusts itself (electric motors . . . ).

A Variant B may proceed as follows: The customer has the data ready (smartwatch, smartphone, chip . . . ). The customer in this case may use any gym (worldwide) that is able to evaluate this data or has the appropriate devices (user engagement . . . ).

In both variants, the data from the fitness equipment may also be transmitted to the "memory" and evaluated. The customer may process the data at home. Based on the data, the utility profile may be refined (adaptively).

During training, it is possible for the force (torque) and/or speed of travel to be adapted not only during movement but also during the number of movements (e.g., increasing force). This is preferably dependent on e.g. the state of fatigue, the profile of the user, the heartbeat and/or blood pressure, etc. It may also be dependent on the lever ratios of the machine and the user (flexion angle of the limbs . . . ). The number of movements and the energy used may also be displayed/output.

In all configurations, braking may be applied either only in one direction or in both directions. A constant force may also be generated by means of storage (pump with accumulator). This or everything may also be done alternatingly. The left and right sides may be treated differently. Specific positions (bending angle, postures . . . ) may be loaded differently than others, if e.g. an injury is present, or may not be loaded in this position under certain circumstances.

In the case of rehabilitation, this has a particular use:

Coordinated training is very important, particularly with users with/after health challenges and/or problems.

The greater the deficit from the standard that results from an accident/illness, the more important is the targeted training. Targeted means here: precisely adapted to the muscle/body impairment. For example, a (older) patient may after a stroke usually only carry out minimal training with regard to strength, duration and mobility, while a trained (professional) athlete has a completely different training spectrum after e.g. a broken leg. For example, an injured left knee must/should be loaded differently from the healthy right knee when training on the same training equipment (e.g. ergometer or home exercise bike). This may be considered individually in the case of the training equipment with the MRF damper.

For example, early mobilization is possible in the normal ward or even in the intensive care unit.

Adaptive and intelligent therapy actuators/training equipment are possible that enable or even automate early mobilization.

After a stroke or similar, certain body parts or halves of the body are usually more affected than other regions. Therefore, it is important that the less powerful limbs/muscles are loaded differently and in particular with a smaller force. This allows a different force-over-distance or torque-over-angle progression to be used. The tension and compression steps may also differ. So in total, the best possible result may be achieved or the patient is not overloaded and thus does not lose the pleasure of training. Here, the recovery progress may also be logged (sending the data to the insurance provider or a cloud service for evaluation).

There is also training equipment has been realized, which may be referred to as a smart hand trainer.

Figure 11:
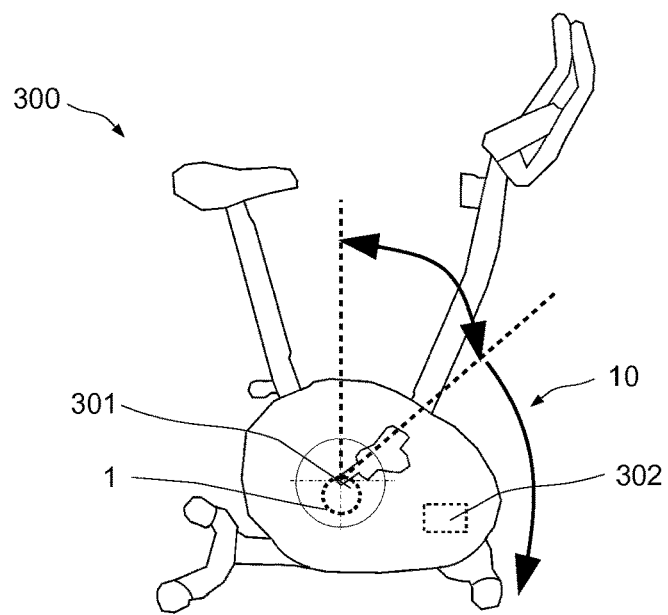
FIG. 11 training equipment or fitness equipment.

FIG. 1 shows a schematic perspective view of a damping system 10 and a rotational damper 1 for the training equipment or fitness equipment 300, e.g. illustrated in FIG. 11.

In this case, the individual parts of the rotational damper 1 are shown in FIG. 1.

The rotational damper 1 is substantially formed from the components 2 and 3, and the pivot shaft 4 is arranged or formed on the component 2. The pivot shaft 4 has a first end 31 and a second end 32. Around the circumference of the component 2, a plurality of arms 21, 22 and 23 may be seen, which will be discussed in more detail in the description of FIGS. 3 to 5.

A driver 4a (for example a fitted key) may be arranged on the pivot shaft 4 in order to rotatably connect the component 2 with a part to be damped. Instead of the key, a spline, polygon connection or another non-positive or positive connection may also be used. During assembly, the component 3 is pushed over the component 2 and finally screwed to the cover 3a, wherein the first end 31 of the pivot shaft 4 extends outward from the right end of the component 3. Spacers 38 may be used for compliance with predetermined distances.

Two variations are basically possible here, namely that the second end 32 of the pivot shaft extends on the other side of the component 3 to the outside, or that the second end 32 of the pivot shaft 4 is mounted in the interior of the component 3 and e.g. in the bearing 37 of the cover 3a of e.g. aluminum or the like. The bearing 37 may be a low-cost slide bearing, but also in the case of high or very high requirements in terms of base friction and lifespan, it may be a ball or roller bearing. If requirements are slight, it may also be omitted.

A rotary encoder or angle sensor 17 is used to detect the angular position of the components 2 and 3 relative to each other. The angle sensor 17 may include a magnetic stack and may be read contactlessly from outside the housing 30. The sensors may also be mounted on coupling elements or operatively connected parts. Instead of a rotary measuring system, a linear measuring system may also be used.

The connecting lines 14 supply the rotational damper 1 with electrical energy.

Furthermore, from left to right are shown a collar, a shim, an addition collar, seals and bearings, spacers etc.

The components 2 and 3 may also have a conical shape. The damping gap 6 need not be equal or uniform over the axial extent 16.

Figure 2:
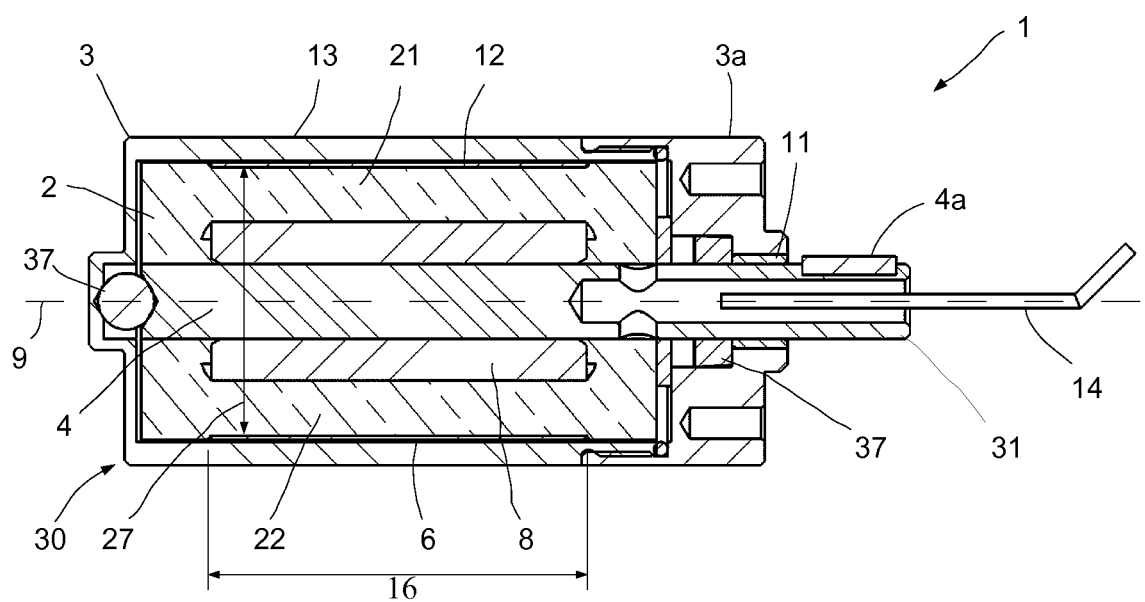
FIG. 2 a schematic cross section through the rotational damper of FIG. 1.

FIG. 2 shows a schematic cross-section in the assembled state, wherein it may be seen that in the assembled state, the component 3 forms a housing 30 of the rotational damper 1. The component 3 accommodates the essential part of the component 2 within itself, so that after the screwing of the cover 3a with the component 3, only the first end 31 of the pivot shaft 4 protrudes out from the housing 30. At the outwardly projecting part of the pivot shaft 4, the driver 4a is arranged. The component 3 has an outer component 13 and forms the housing 30. The component 2 has an inner component 12, which is surrounded by the outer component 13.

The pivot shaft 4 is mounted in the vicinity of the first end 31 via a bearing 37 and at the other end 32, a spherical bearing 37 is furnished so that the pivot shaft 4 protrudes to the outside in only one place. As a result, the base friction and thus the base torque may be reduced, whereby a higher sensitivity and better response of the rotational damper 1 under load may be achieved.

A geometric axis 9 extends centrally through the pivot shaft 4. The electrical connecting lines 14 extend through the pivot shaft 4, which are fed in from the outside (without a slip ring) through the pivot shaft 4 to the electric coils 8 that are arranged in the interior of the housing 30.

In the highly schematic cross section of the rotational damper 1, two arms 21, 22 may be seen on the inner component 12 of the component 2.

The damping gap 6 is furnished radially between the inner component 12 and the outer component 13 and extends over an axial length 16 which has a substantial portion of the length of the inner component 12. The length 16 of the damping gap 6 is preferably at least half and in particular at least ⅔ of the length of the component 3.

Particularly in the case of large diameters 27 of the damping gap 6, it is possible to respectively furnish seals at the axial ends of the damping gap 6 in order to keep the magnetorheological medium substantially, and preferably completely, within the damping gap 6. In simple configurations, a magnetic seal may be furnished in which the very thin gap still existing between the components 2 and 3 is magnetically sealed.

At least one seal is furnished at the outlet of the thinnest possible pivot shaft 4 from the housing 30. Here, the seal 11 is furnished between the pivot shaft and the corresponding passage opening in the cover 3a.

Without a separate seal at the axial ends of the damping gap 6, the base friction is very low. The volume of the magnetorheological medium is determined by the volume of the damping gap 6 and the approximately disc-shaped volumes at the two axial end faces between the inner component 12 and the outer component 13, and is low overall.

The volume of the damping gap 6 is very small, because the radial height of the damping gap is preferably less than 2% of a diameter 27 of the damping gap which in this case is cylindrical. The radial height of the damping gap is in particular less than 1 mm and preferably less than 0.6 mm and particularly preferably less than 0.3 mm. With a length 16 of, for example, up to 40 or 50 mm and a diameter 27 of up to 30 mm and a gap height in the range of 0.3 mm, a gap volume of <2 mL results; in consequence, the production costs may be kept very low. The volume of the magnetorheological medium is in particular less than 3 ml and preferably less than 2 ml.

Between pivot shaft 4 and the element to be damped, it is also possible to arrange a transmission according to the prior art, preferably a planetary gearing as free as possible of backlash, a microgear or a wave gearing (e.g. harmonic gearing).

Instead of a direct connection or a connection via a coupling rod, a disc may also be mounted on the input shaft. The disc or the disc outer diameter may be connected (positively or non-positively) via at least one cable or belt with the element to be damped. The connecting element may also be operatively connected with the element to be damped via deflections, translations (e.g., pulley principle . . . ). As a result, the structure with respect to the attachment is very flexible. But an eccentric disc or cam may also be used, in which case the forces/torques are dependent on angular position. A circulating rope with fixing point may also be used, which makes possible a positive control, i.e., tensile and compressive forces may be transmitted. The transmission element (e.g. the cable) may be positively or non-positively connected with the disk.

Figure 3:
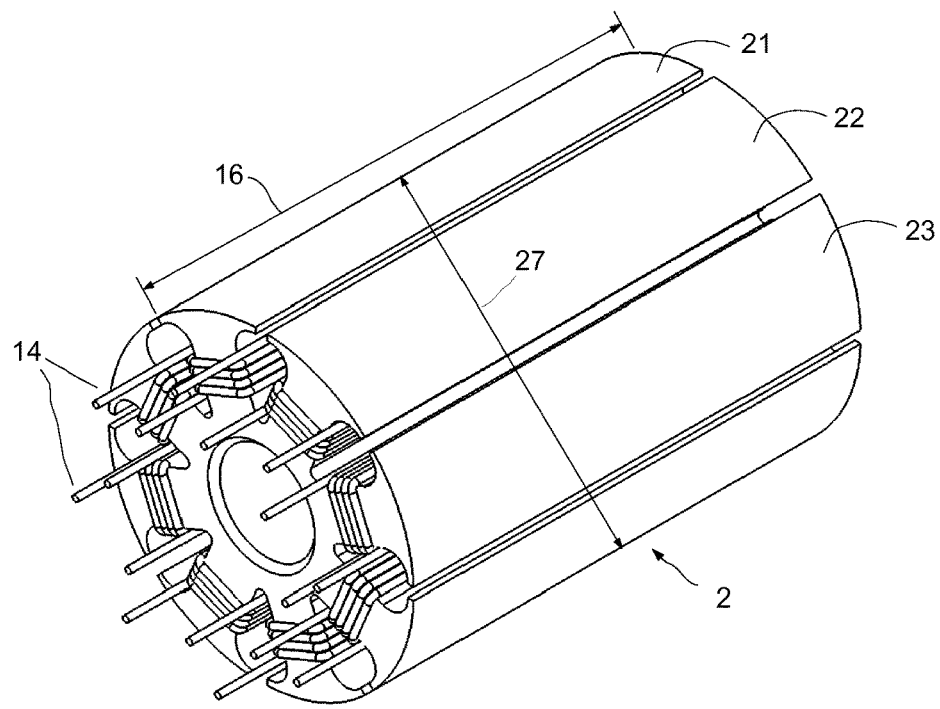
FIG. 3 a perspective view of a portion of the rotational damper of FIG. 1.

FIG. 3 shows a schematic perspective view of a portion of the rotational damper 1, wherein the component 2 is shown without the pivot shaft 4. During assembly, the illustrated part of the component 2 is rotatably coupled to the pivot shaft 4.

The component 2 has a plurality of radially outwardly projecting arms 21, 22, 23, etc. In this case, eight arms are furnished. However, 6 or 10 or 12 or more arms are possible and preferred.

A coil 8 is respectively wound around the respective arms with at least one and in this case a plurality of windings. In this case, the winding and the connection of the electric coils are made in such a way that different poles of the magnetic field result at adjacent locations of adjacent arms when the coils 8 are supplied with current.

Figure 4:
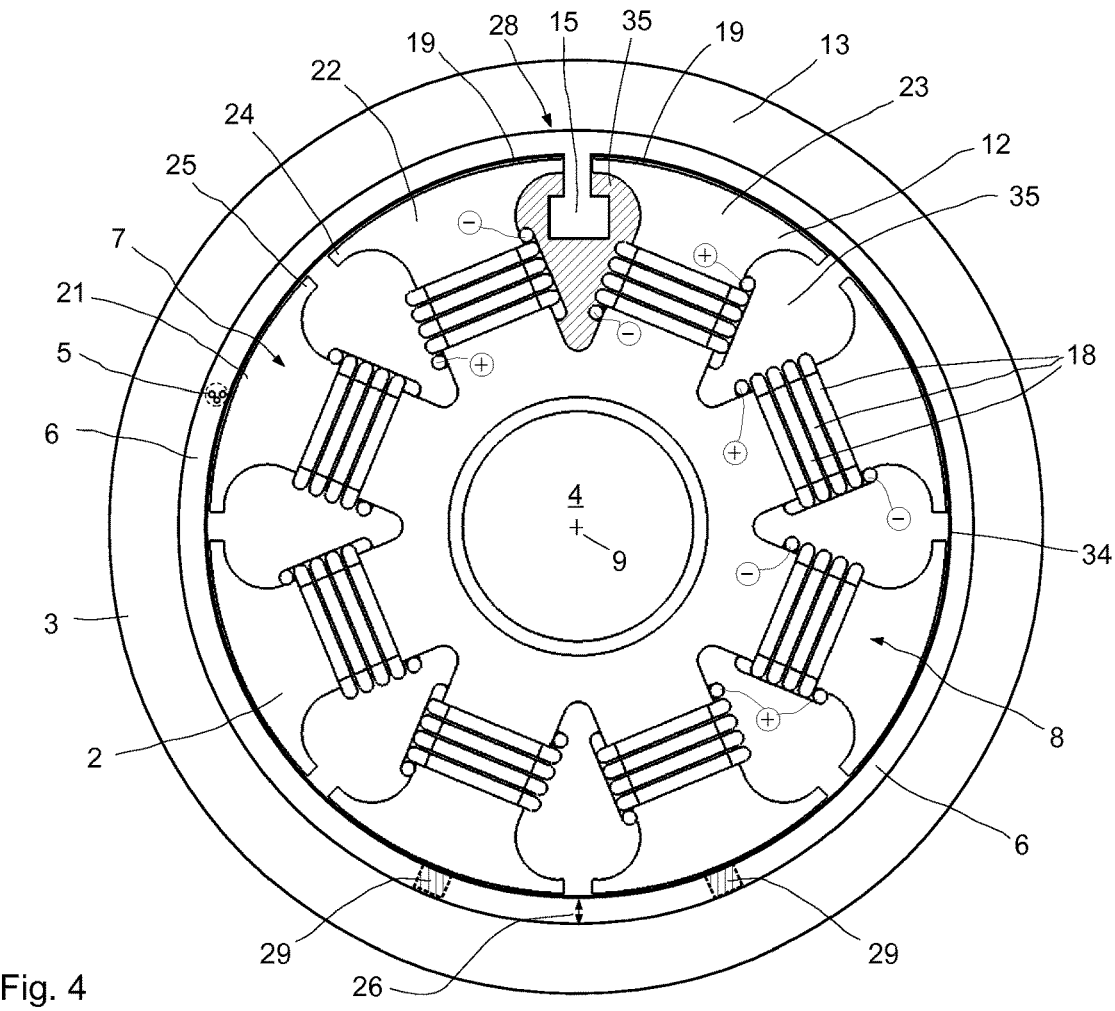
FIG. 4 a schematic cross section through the rotational damper of FIG. 1.

FIG. 4 shows a cross section through the rotational damper 1, wherein the component 2 has the inner component 12, which is surrounded by the outer component 13 of the component 3. Between the two components 2 and 3 in this case, there extends a substantially cylindrical damping gap 6, in which a magnetorheological medium 5 is present. In particular, the damping gap 6 is completely filled with the magnetorheological medium 5. At least one reservoir 15 may be furnished in which a supply of the magnetorheological medium is stored in order to be able to compensate for the loss of a certain amount of the medium over the lifespan of the rotational damper 1. Such a reservoir 15 may be furnished, for example, in the recess between two arms 22, 23. The reservoir may also be outside the component 3.

During manufacture, the coils 8 are first wound around the individual arms. Subsequently, the remaining cavities between the individual arms may be partially or completely filled with a medium, so that no magnetorheological fluid may be filled thereinto. For example, casting resin or the like may be filled therein to fill the cavities. Casting resin or the like is less expensive than the magnetorheological fluid. The filling of cavities is not necessary from a functional standpoint. But it is also possible that a thin protective layer, for example, in the form of a cover 34, is coated in order to locally limit the damping gaps 6, while the recesses between the arms remain hollow.

Preferably, the damping gap is cylindrically shaped. But it is also possible that separating elements 29 are arranged in the coupling gap, which divide the cylindrical coupling gap into a plurality of partial gaps. In this case, the separating elements 29 are preferably connected to either the component 2 or the component 3.

The coupling gap 6 may itself form the chamber 28 for the magnetorheological medium or else the coupling gap 6, together with the reservoir 15, may form at least the essential part of the chamber 28.

Figure 5:
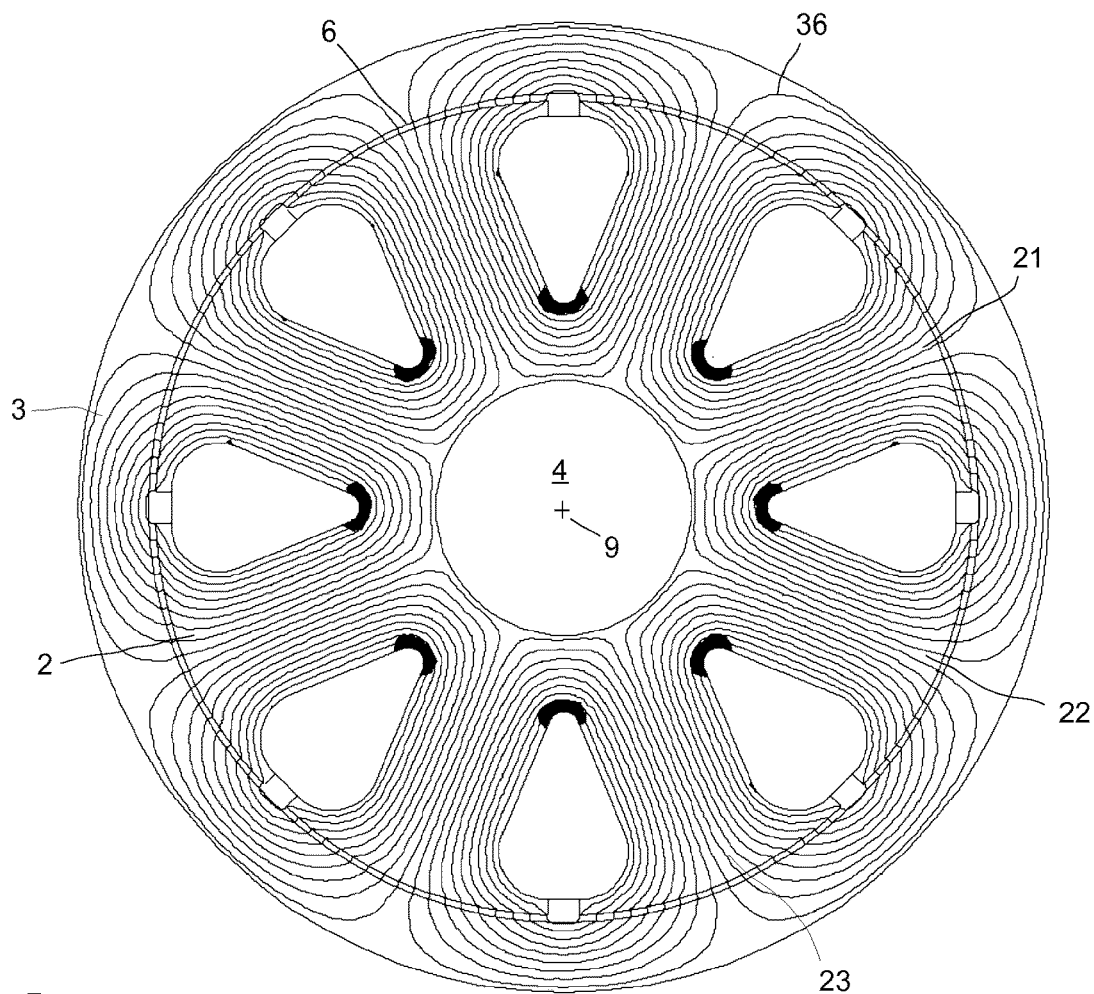
FIG. 5 schematically drawn magnetic field lines in the rotational damper of FIG. 4.
Figure 6:
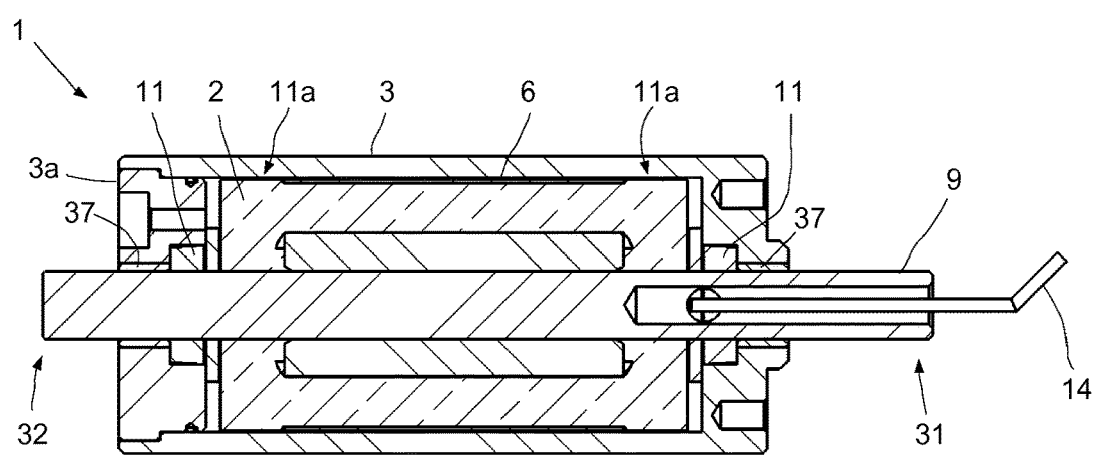
FIG. 6 a cross section through a further rotational damper.

FIG. 5 shows a highly schematic view of a field line profile over the cross section of the rotational damper 1 from FIG. 6. In this case, the field lines 36 pass approximately radially through the damping gap 6, respectively extending through the component 3 over an angle section before they re-enter the adjacent arm approximately perpendicularly through the damping gap 6 (into the adjacent arm).

Illustratively, FIG. 5 shows that there is a high field line density over practically the entire circumference of the rotational damper, so that an effective damping of a pivoting movement is made possible.

FIG. 6 shows a further configuration of a rotational damper 1 for training equipment 300, in which the functionality is basically the same as in the case of the foregoing rotational damper 1. In contrast to the foregoing configurations, in the rotational damper 1 according to FIG. 6, the pivot shaft 4 extends to the outside both at the first end 31 and at a second end 32. Accordingly, the pivot shaft 4 is mounted at both ends and sealed to the outside by seals 11. Here too, magnetic seals 11a may re-seal the damping gap 6 in the axial directions.

The pivot shaft 6 may be implemented standing, in this as well as the other embodiments, i.e., as an axis, in which case the housing 3 pivots with a damping effect and is operatively connected to the element to be damped.

Figure 7:
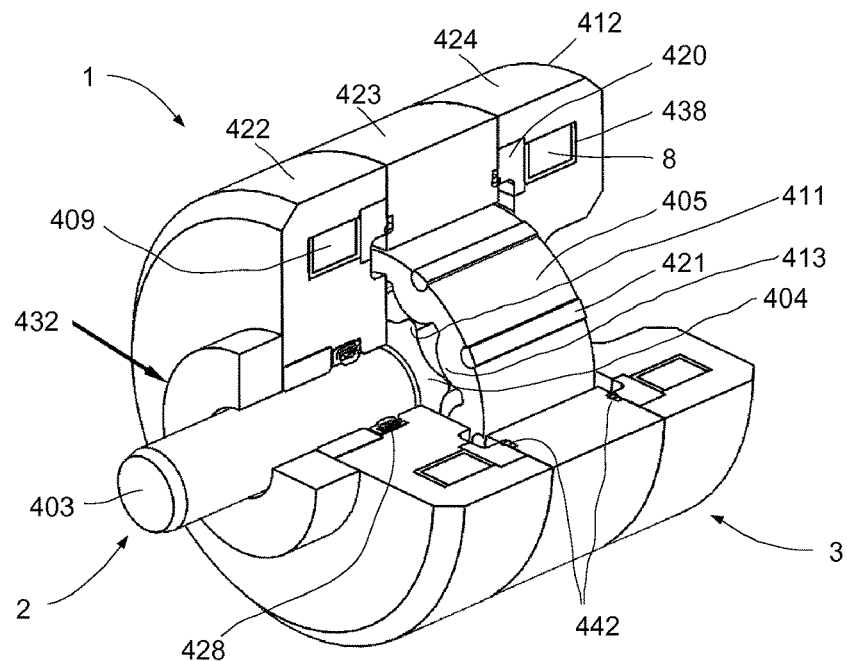
FIG. 7 a schematic perspective partial cross section of a rotational damper for fitness equipment according to the invention.
Figure 13:
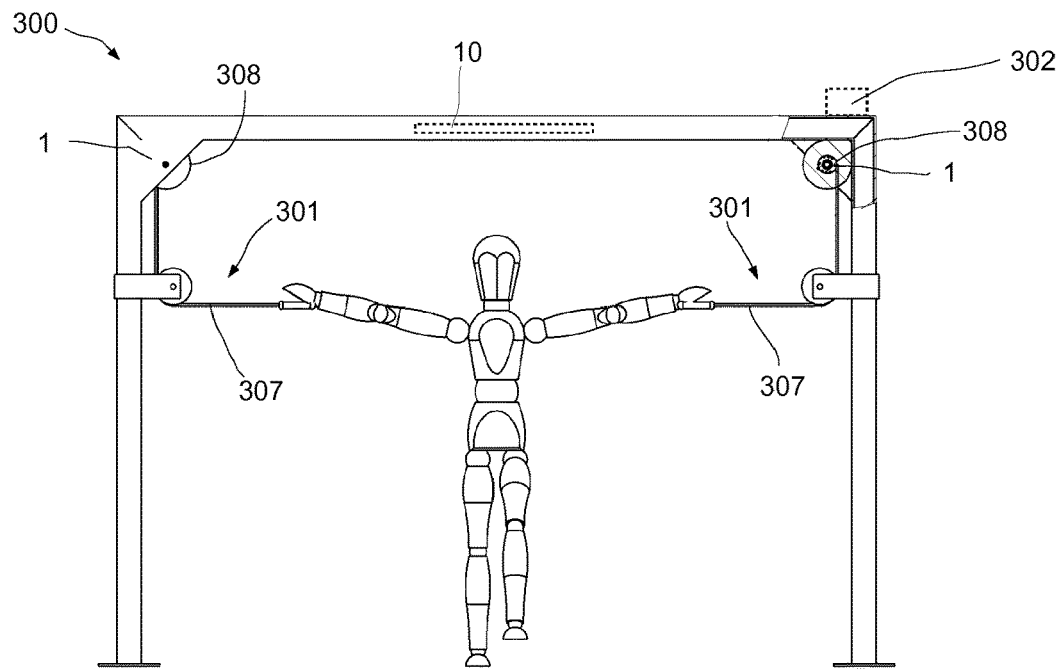
FIG. 13 further training equipment or fitness equipment.
Figure 14:
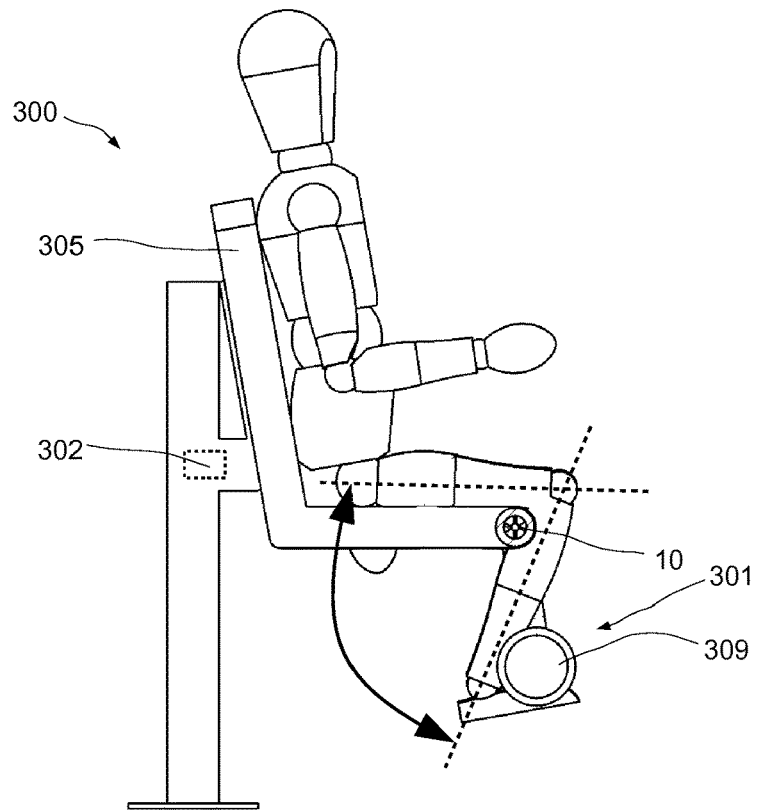
FIG. 14 another training equipment or fitness equipment.

FIG. 7 shows a rotational damper 1 of fitness equipment 300 e.g. from FIG. 11, 13 or 14.

FIG. 7 shows a partial section of the rotational damper 1, wherein may be seen an external toothing 411 of the first displacement component 404 and also the internal toothing 413 of the second component or displacement component 405. Inside, a magnetorheological medium or fluid is furnished or the interior is substantially filled with a magnetorheological fluid, which may be exposed to a magnetic field 408 with the electric coils 8.

Here it may be seen that the housing 412 of the rotational damper 1 comprises three sections, namely a first end area 422, a central area 423 and a second end area 424. Here each area is formed by a separate part. It is also possible that even more parts are furnished, or that only a total of two housing halves are furnished.

The housing forms a component 2 or 3 and the damper shaft 403 forms the other component 3 or 2. A rotational movement of the components 2 and 3 relative to one another is damped in a controlled manner in order to set the damping force that will be necessary at the corresponding time in the training equipment 300.

In the housing 412 of the rotational damper 1, one electrical coil 8 is respectively received in a coil holder 438 in the left-hand end area 422 and in the second right-hand end area 424.

Axially adjacent to each electric coil 8, a ring 420 is furnished, wherein the rings 420 are arranged between the two coils 8 and respectively adjoin the central area 423 from the outside. The rings 420 are arranged axially adjacent to the electric coils 8 to prevent a magnetic short circuit there.

At the damper shaft 403, an angle sensor 432 is furnished, which may be embodied for example as an absolute rotary encoder. The damper shaft 403 is sealed to the interior 416 by a seal 428. Circumferential seals 442 are arranged between the housing parts of the different areas in order to prevent the escape of magnetorheological fluid from the interior of the displacement device 402 to the outside.

The second displacement component 405 with an overall approximately cylindrical outer shape has a plurality of guide units 421 on the outer circumference, which extend here in the exemplary embodiment over the full axial length, but in other embodiments may for example also be shorter. The guide units 421 project radially outwardly beyond the second displacement component 405 or the core material of the second displacement component 405, and provide a defined radial distance between the outer surface of the core material of the second displacement component 405 and the inner circumference of the housing 412 in the central area 423.

Figure 8:
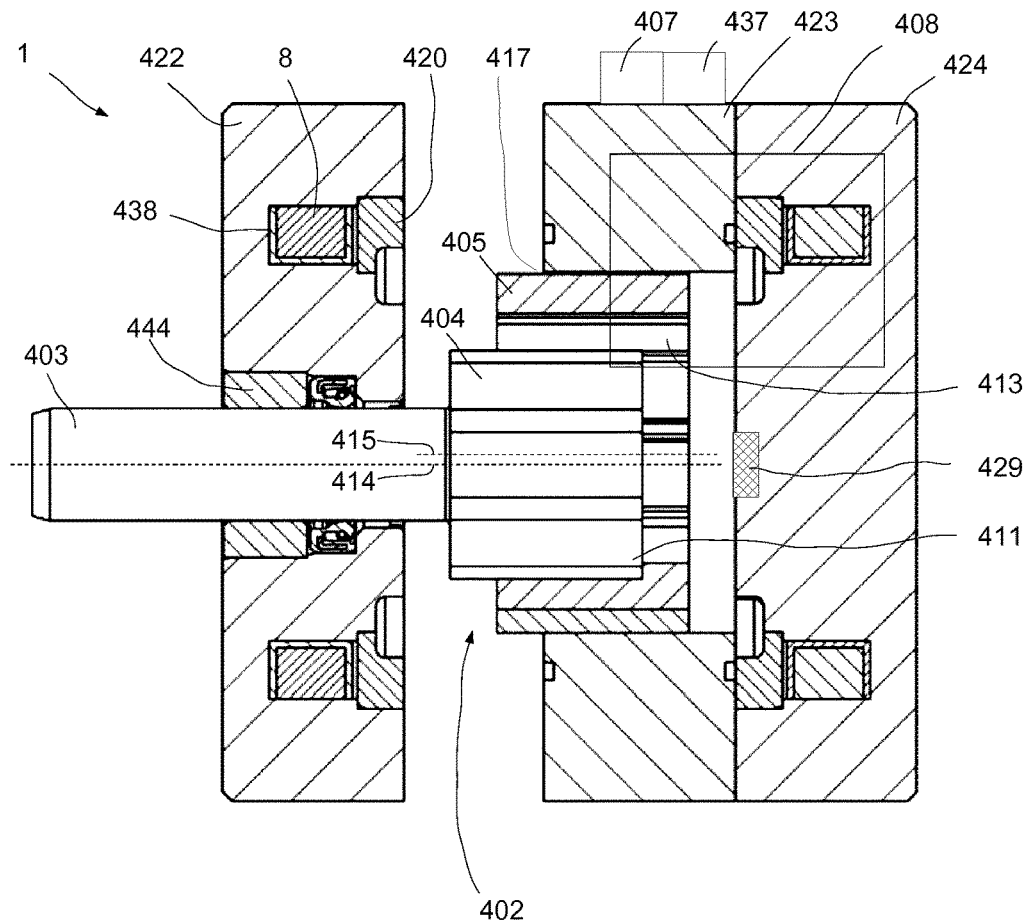
FIG. 8 a section through a partially exploded view of FIG. 7.

FIG. 8 shows an exploded view of the rotational damper 1 in section, wherein the left housing part with the first end area 422, and the first displacement component 404 and the second displacement component 405, are shown respectively arranged offset a distance axially to allow a better understanding of the technical functionality.

The damper shaft 403 is here formed in one piece with the first displacement component 404, which has on its outer circumference an external toothing 411 which meshes with an internal toothing 413 in the interior of the second displacement component 405. The second displacement component 405 is surrounded radially by a damping channel 417, through which the magnetorheological fluid conveyed inside the second displacement component 405 may flow back to the axially opposite side.

On the outside, the control system 407 is shown, which may be supplied with the necessary power via an energy storage 437 or rechargeable battery or the like, even if an electrical power supply fails.

A compensation volume 429 is always available in order to provide a volume compensation at different temperatures.

The damper shaft 403 is supported by a bearing 444. The rotational axis 414 of the first displacement component 404 coincides with the rotational axis of the damper shaft 403. The rotational axis 415 of the second displacement component 405 is offset parallel thereto.

A fitness equipment 300 with a rotational damper 1 according to FIGS. 7 and 8 or with a plurality of rotational dampers (identical or different) offers outstanding properties and may either generate or reduce high torques. Setting, and any change in the damping strength, may be done at any time in real time. The damping may be adjusted based on at least one training parameter.

The rotational damper 1 according to FIGS. 7 and 8 has a displacement device 402. The displacement device 402 has a damper shaft 403 and intermeshing and in particular rotating displacement components 404 and 405. In this case, a rotational movement of the damper shaft 403 is controlled and may be damped in a controlled fashion. The displacement device 402 contains a magnetorheological fluid as the working fluid. At least one control system 407 is associated therewith. Furthermore, at least one magnetic field source is furnished or comprised, having at least one electric coil 8. The magnetic field source may be controlled via the control system 407 and the magnetorheological fluid may be influenced via the magnetic field, in order to adjust a damping of the rotational movement of the damper shaft 403.

Such a rotational damper 1 is very advantageous in fitness equipment 300. One advantage is that the displacement device 402 is equipped with a magnetorheological fluid as working fluid. As a result, under the control of the control system 407, the magnetic field of the magnetic field source is adjusted in real time, i.e. within a few milliseconds (less than 10 or 20 ms) and thus the applied braking torque on the damper shaft 403 is also adjusted in real time when the fitness equipment 300 is supposed to yield a corresponding braking torque. The structure of the rotational damper 1 is simple and compact and requires few parts, so that the rotational damper 1 may be manufactured inexpensively and may be integrated into the fitness equipment.

The displacement device 402 is designed in particular as a type of compressor device or pump. The displacement device 402 has intermeshing displacement components 404 and 405 which rotate in operation. Inside the displacement device 402, a displacement chamber is furnished, which may also be referred to as a compressor chamber.

The interior or interior chamber of the displacement device contains a magnetorheological fluid as the working fluid.

A liquid pressure sensor may be used as a sensor that detects the pumping pressure. By this means, the torque and/or force introduced may be derived and used as a characteristic in the control system or the training algorithm.

Figure 9:
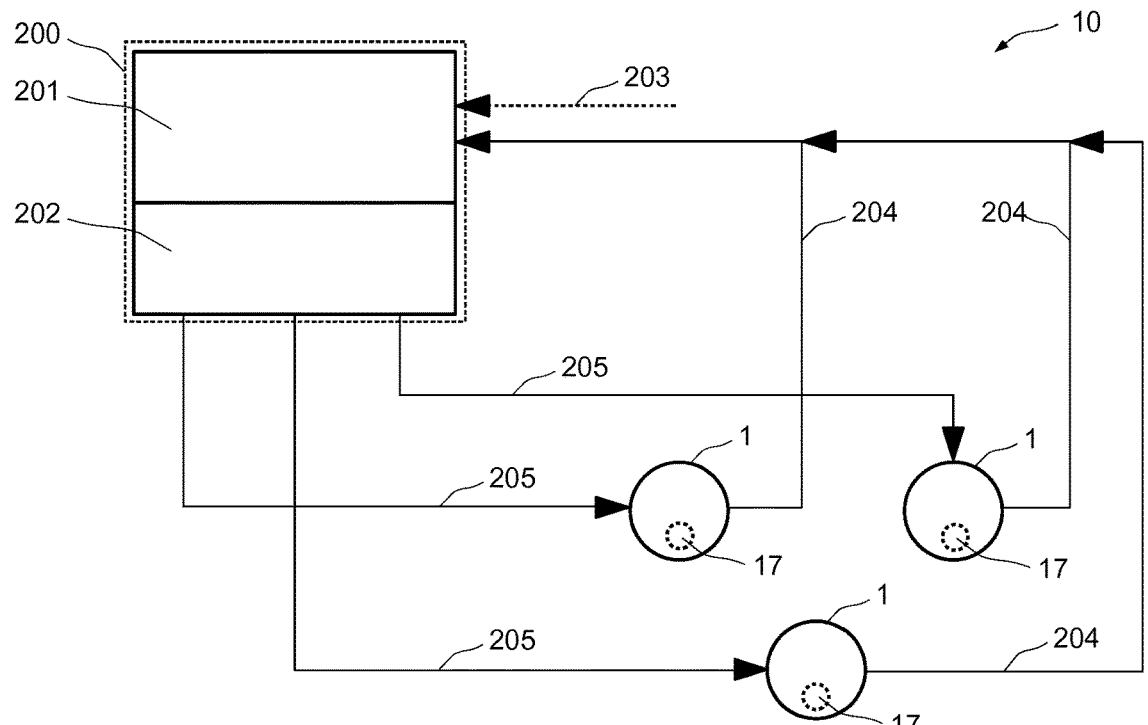
FIG. 9 a highly schematic sketch of the control of the damping system.
Figure 10:
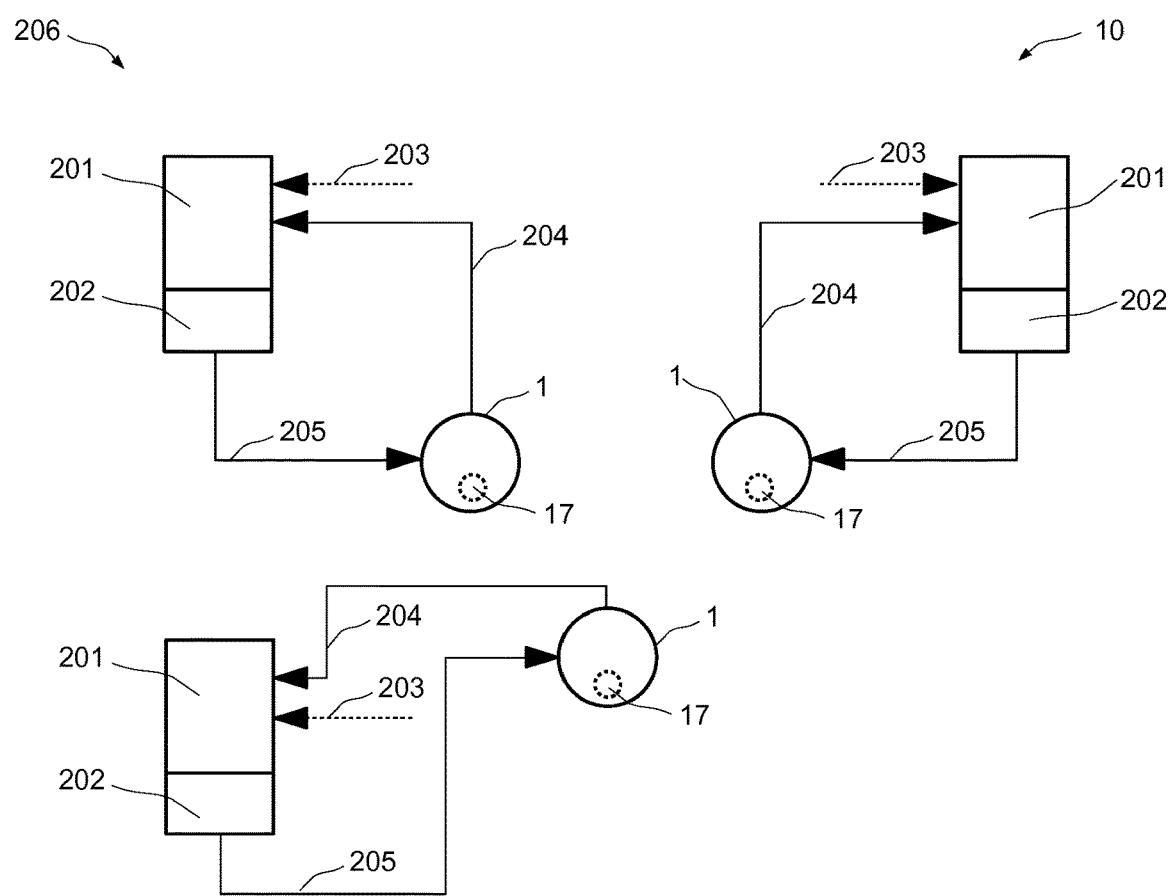
FIG. 10 a highly schematic sketch of a further configuration of the control of the damping system.

FIGS. 9 and 10 show highly schematic exemplary embodiments of a control system of the damping system 10 of a fitness equipment 300 (or a plurality of such pieces of fitness equipment 300).

In the context of the present invention, the term "control" also refers to regulation, so that the control system is preferably also suitable and designed for regulation.

As an example, only three interconnected rotational dampers 1 are shown here as actuators. But there may also be furnished four or five or even 10 or a multiplicity of controlled actuators. It is also possible, however, that only one or two actuators are furnished.

The dampers 1 are operatively connected to a computation unit 201. The computation unit 201 receives for each damper 1 respectively at least one actuator signal 204, which describes at least one characteristic magnitude of at least one state of the damper 1. For example, an actuator signal comprises a characteristic magnitude which is detected by the rotary encoder 17. The actuator signal may also include a characteristic magnitude that is detected by at least one torque sensor and/or at least one current sensor. Other suitable sensor types are also possible. Particularly preferably, the computation unit 201 takes into account a plurality of actuator signals 204 that originate from different sensors.

Preferably, the computation unit 201 also takes into account at least one item of system information 203 which describes at least one system variable. The system information 203 comprises, for example, acceleration values of the drum 101 and/or the drum housing 109 and/or other system magnitudes.

Based on the provided actuator signals 204, the computation unit 201 respectively determines at least one characteristic for an optimal resistance torque for the damper 1. The characteristics for the determined resistance torques of the actuator of the damper 1 are each respectively provided to a current/torque regulator 202 associated with a damper 1.

The current/torque regulator 202 outputs at least one control voltage 205 for each damper 1 respectively based on the resistance torques provided. Also possible are control signals with other and/or additional magnitudes suitable for controlling the damper 1, such as the voltage. The respective damper 1 is set based on the control voltage 205.

The control shown in FIG. 9 is configured as a central controller 200. In this case, the central controller 200 comprises the computation unit 201 and the current/torque regulator 202 associated with the respective dampers 1.

In a configuration not shown here, the current/torque regulator 202 associated with the respective dampers 1 may also be configured in a decentralized fashion. The computation unit 201 remains centralized in that case. For this purpose, the current/torque regulator 202 is arranged in particular separately and spatially separated from the computation unit 201.

In FIG. 10 a control is shown that is configured as a decentralized control 206. In this case, the dampers 1 are each respectively assigned at least one own computation unit 201 and at least one own current/torque regulator 202. It is possible for the computation unit 201 assigned to a damper 1, and the current/torque regulator 202, to be designed to act autonomously. However, a configuration is also possible in which the decentralized control 206 also takes into account system information 203.

FIG. 11 shows training equipment 300 or fitness equipment apparatus with a damping system 10 according to the invention. In this case, the training equipment 300 is designed as an ergometer or exercise bike. The equipment comprises a muscle-powered actuating element 301, which is designed here as a pedal crank device with a pedal and a bottom bracket. In this case, the movement of the actuating element 301 may be damped by the rotational damper 1.

The damping characteristics of the rotational damper 1 may also be adapted several times during a single revolution. In particular, the torque is adapted that is required for rotating the actuating element 301. A control system 302 is furnished for setting the damper 1 in this case.

FIG. 11 shows training equipment 300 having a damping system 10. In this case, the training equipment 300 is designed as an ergometer or exercise bike. The equipment comprises a muscle-powered actuating element 301, which is designed here as a pedal crank device with a pedal and a bottom bracket. In this case, the movement of the actuating element 301 may be damped by the rotational damper 1. A control system 302 is furnished for setting the damper 1 in this case.

The damping characteristics of the rotational damper 1 may also be adapted several times during a single revolution. In particular, the torque is adapted that is required for rotating the actuating element 301. The torque is thus furnished as a training parameter. The torque may also be adapted depending on the angle of rotation. The angular position or angle of rotation is indicated here by two dashed lines and a double arrow. The direction of rotation is marked by an arrow.

The control system 302 controls the field generation system here in such a way that a specific damping force must be applied for the movement of the components 2, 3 which are movable relative to one another. In this case, the control system 302 takes into account the predetermined training parameter(s). For example, if a specific torque is given, the control system 302 sets the damping force in such a way that the training user may rotate the pedal drive only at the predetermined torque.

An angular speed or cadence that the training user must achieve may be predetermined as a training parameter. The damping force may in this case be set to a basic value or to a value set by the trainer. The training user must then reach the predetermined cadence with this torque.

If the cadence defined as the training parameter is reached over a defined period of time or is exceeded by a defined value, the control system 302 may increase the damping force by a defined value. For this purpose, the control system 302 monitors the cadence as a characteristic by means of a sensor device, not shown here, and also takes this into account when setting the damping force.

Reaching or exceeding the required cadence indicates that a specific training condition has been reached. Thus, the control system may now independently adapt the damping force, so that the training user must achieve the required cadence at a higher torque. Particularly good training results may be achieved by means of such adaptive or intelligent adaptation.

Likewise, the required torque or damping force may be reduced if the training user does not reach the cadence that has been set as a training parameter even after a specific period of time.

The training equipment 300 shown here also provides an adaptation of the damping force during a single actuation of the actuating element 301. A single actuation in this case means a single revolution of the pedal drive.

For example, the damping force may be reduced when the pedal drive is in a dead center position. It is also possible that the damping force may be increased when the pedal position is in a lever position that is optimal for the training user, or is or outside the dead center.

The damping force or torque may also be varied during a single actuation of the actuating element 301, resulting in a low body load (joint load, muscle load). The damping force or torque may also be varied during a single actuation of the actuating element 301 in such a way as to yield the best possible training result/outcomes (increased endurance, muscle gain, good fat burning).

The damping force, or damping torque, may also be varied during a single actuation of the actuating element 301, to give a user-selected combination of body loading and training result/outcome. All this may also be further optimized or adapted by distinguishing and adapting between left and right halves of the body (e.g. left or right leg) during a single actuation.

This is achieved in this case in that the control system 302 adjusts the damping force and thus adjusts the torque based on the angular position of the actuating element 301 or pedal drive. For this purpose, the angular position of the actuating element 301 is preferably detected continuously by sensor means as a characteristic during pedaling.

Figure 12:
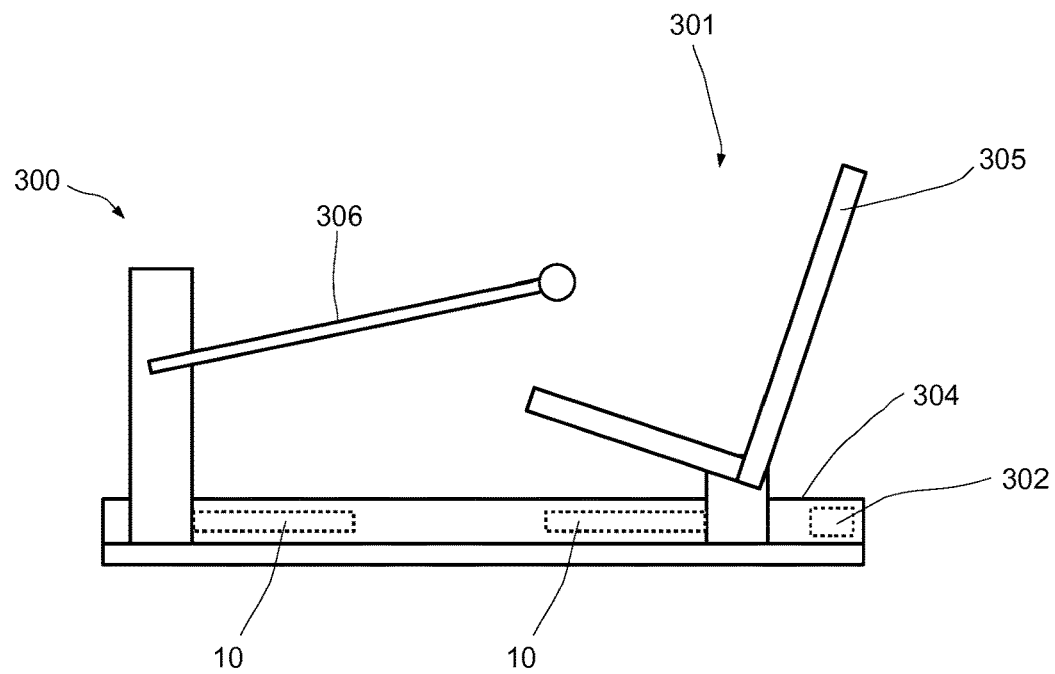
FIG. 12 further training equipment or fitness equipment.

FIG. 12 shows a configuration of the training equipment 300 as a rowing machine. The actuating element 101 is in this case configured as the seat 305 or the oar 306. In this case, the seat 305 is displaceably mounted on a frame 304. The oar 306 is likewise fastened to the frame 304. In an alternative configuration, the oar 306 may also be movably or displaceably accommodated on the frame 304.

The movement of the seat 305 is damped in this case by means of a damping system 10 with a linear damper. The movement of the oar 306 may also be damped via a damping system 10.

The force required to pull the seat 305 to the oar 306 may for example be adjusted as a training parameter in this case. The control system 302 then adjusts the damping force correspondingly. A different damping force may be furnished for forward movement than for backward movement. In this way, the rowing movement may be simulated particularly well.

In addition, the path may also be predetermined as a training parameter that the seat 305 may travel in a rowing stroke. In doing so, the control system 302 may detect by sensor means the position of the seat 305 with respect to the frame 304 and may adjust the damping force as a function of the seat position. In this way, when the seat has been advanced by a predetermined length, set as a training parameter, in the direction of the oar 306, the mobility of the seat 305 may be completely blocked by a correspondingly high damping force. As a result, a faulty posture during rowing training may be avoided. In addition, the rowing movement may be optimally adapted to the height or leg length of the training user.

The training equipment 300 in this case offers the possibility of adaptively varying the damping force during a single actuation of the actuating element 301, taking into account a characteristic. The single actuation of the actuating element 301 is in this case a single rowing stroke. In this case, the speed of movement of the seat 305 along the frame 304 is detected as a characteristic by sensor means. When the speed of the seat 305 reaches or exceeds a threshold value in a single rowing stroke, the damping force for the movement of the seat 305 is increased by a specific value. Likewise, the damping force may be reduced by a specific amount when the seat 305 does not reach a threshold value for a speed of movement once or repeatedly.

FIG. 13 shows a configuration of the training equipment 300 as a cable pull device for training the arms and/or the trunk. The training user pulls with the hands on a respective cable 307 as the actuating element 301. The cables 307 are respectively taken up on a pulley 308. A continuous cable 307 for both arms may also be furnished, which is connected to only one pulley 308. The provision of the cables 307 in this case occurs via a roller spring.

The rotational movement of the pulley 308 when pulling on the cable 307 is damped in this case by a rotational damper 1. In an alternative configuration, the movement of the cable 307 may also take place via a damping system 10 with a linear damper.

The damping for pulling and holding and also leaving the cable 307 in this case may be adjusted separately. Doing so significantly improves the training effect. For example, the cable 307 may be released slowly, in a targeted fashion, by damping. In this way, a spring back via the spring and high holding forces may be avoided for example during rehabilitation exercises. At the same time, however, higher tensile forces are also possible when pulling on the cable 307.

FIG. 14 shows training equipment 300 designed as a leg extension machine. The training user is seated on a seat 305 during training and lifts a leg lever 309 by stretching the legs or knees. The leg lever 309 serves as an actuating element 301 in this case, and is pivotably mounted on the seat 305. The pivoting movement may be damped by a damping system 10. For the damping system 10 in this case, for example, with reference to FIG. 7, 8, there is used a rotational damper 1 or the damper unit 80 according to FIG. 16.

The pivoting angle and the force required to pivot the leg lever 309 are predetermined as training parameters. As a further training parameter in this case, the actuating force of the leg lever 309 is furnished as a function of the angle.

At the beginning of the movement, that is, when the knee is still bent, a damping force adapted to the needs of the training user is set by the control system 302. To avoid disadvantageous loading of the knee, as the knee extension increases, the force required to move the leg lever 109 is reduced. For this purpose, the control system 302 continuously detects the angular position of the leg lever 309 and adapts the damping force based on that angle. The angular position or angle are indicated in this case by two dashed lines and a double arrow.

In addition, the angular range over which the leg lever 309 may be pivoted may also be set as a training parameter. This is especially important in the rehabilitation of knee injuries, because overextension of the knee should be avoided in such cases. For example, the trainer may specify as a training parameter the angular position of the leg lever 309 at which the damping force is increased to a level that will block the mobility of the leg lever 309. For this purpose, the control system 302 monitors the angular position of the leg lever 309.

The training equipment 300 may also adaptively vary the damping characteristic during a single actuation of the leg lever 309, taking into account the characteristic. For this purpose, the control system 302 detects the angular velocity or the movement speed of the leg lever 309 as a characteristic. This prevents the training user from stretching the knee too quickly and thus not achieving the necessary muscle training.

If the control system 302, for example, recognizes a too-fast movement of the leg lever 309, it automatically increases the damping force and thus brakes the disadvantageous movement. It is particularly advantageous that this adaptive adaptation may take place during a single actuation or a single knee extension. Otherwise, even a single overextension may cause pain. It is also particularly advantageous that this adaptive adaptation is performed by the control system 302 itself, and consequently the trainer or therapist does not have to constantly monitor the training user.

If the training user executes the next movement at a correct speed, the control system 302 does not make any adaptation or sets the training parameter unchanged.

The control system 302 may also durably increase or reduce the force required for pivoting the leg lever 309. This may be done if repeatedly too-fast movements of the leg lever 309 are detected by the sensors. In this way, a training parameter may be adapted without the trainer having to track the entire training unit or analyze the recorded characteristics.

Figure 15:
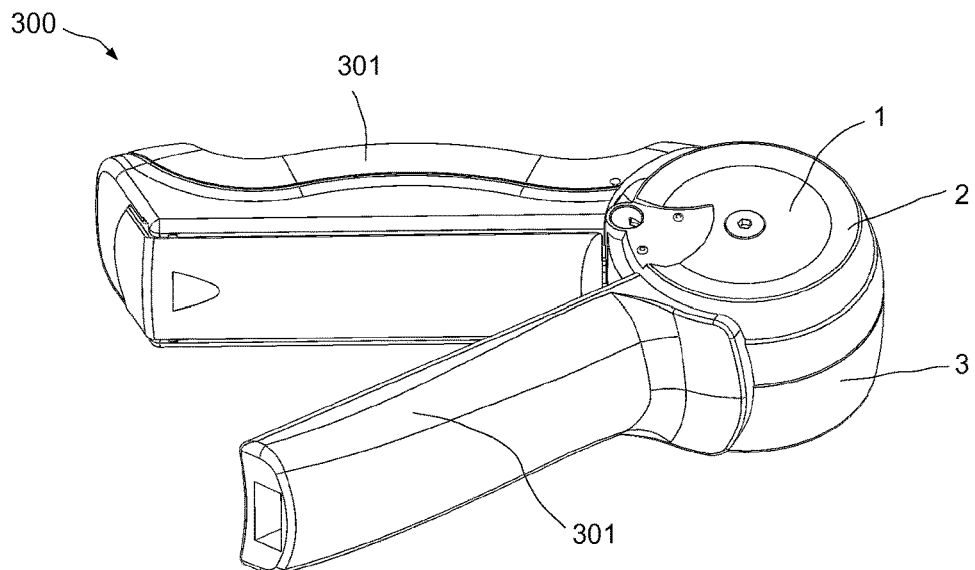
FIG. 15 yet another training equipment or fitness equipment.

Another training equipment 300 and the damper unit 80 inserted therein will be explained with reference to FIGS. 15 to 17. The damper unit 80 may be designed as a rotational damper 1, but may also be realized as a linear damper. FIG. 15 shows a perspective view of the training equipment 300 designed as a hand gripper.

The training equipment 300 includes two actuating elements 301, respectively having an actuating element connected to a component of the damper unit 80. The actuating elements 301 are pivotably connected together. At the pivot joint, a rotational damper 1 is arranged as a damper unit 80.

The torque or the manual force may be varied without intermediate steps by means of the rotational damper 1. The manual force may also be varied over the angle. Tactile grids or ribs, etc., are also possible. The controller may be located internally or externally. Activation may also be done via Bluetooth and a smart device (smartphone, smartwatch . . . ) or computer. Control may also be done via the Internet or a (company-internal) LAN. A program on the computer (also as an app) may serve as the controller. The manual force in this case is set between components 2 and 3.

Figure 16:
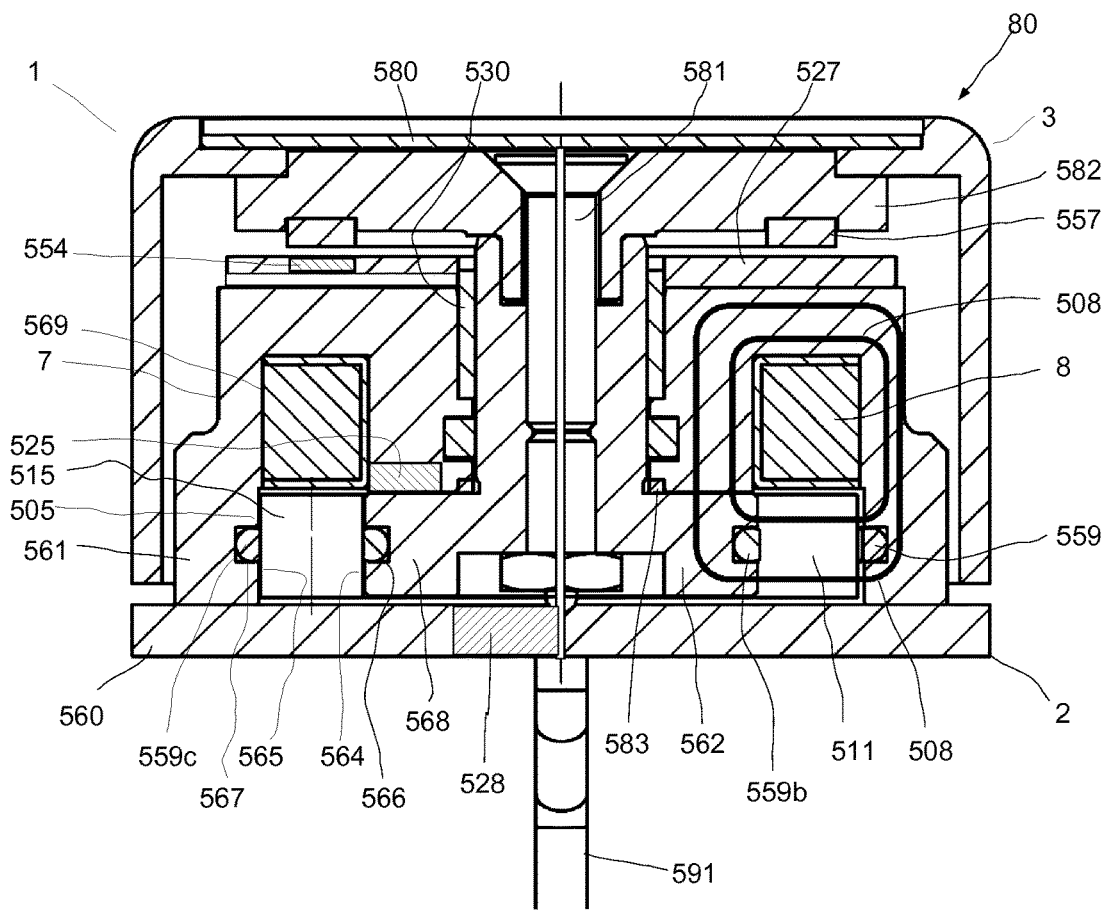
FIG. 16 a damper for the training equipment of FIG. 15 in section.

FIG. 16 shows a schematic cross-section of a rotational damper 1 of the training equipment 300, wherein the rotational damper operates on a magnetorheological basis, the operating principle of which will be explained with reference to FIG. 17.

FIG. 16 shows a cross section, with the component 2 connected to the base body, across from which the component 3 is rotatably accommodated. The base body has a receiving housing 561, which is fastened to a separate base plate 560. For example, the receiving housing 561 may be glued to the base plate 560 after the parts arranged therein have been assembled. The component 3 is rotatably or pivotally received relative to the base body. The component 3 in this case comprises a shaft 562 to which a holder 582 is screwed by means of a screw 581. An internal display unit surrounded by the component 3 may also be accommodated on the holder 582. As a result, the components may be rotated against each other and the display unit remains visible. However, it is preferred to provide a display on an external device and to transmit the necessary data there via a wired or wireless interface.

The shaft 562 is rotatably mounted on the receiving housing 561 via a bearing 530. The bearing 530 may for example be designed as a friction bearing, but may also comprise a different roller bearing.

In the interior, a ring-shaped receiving space 569 is furnished in the component 2 and more precisely in the receiving housing 561, which is filled in this case by an electric coil 8 as the field generating device 7. Any possible clearances may be filled by, for example, a joint compound or a filler, which also serves to hold the electric coil 8 in the ring-shaped receiving space.

It is possible, as shown on the left side of FIG. 16, that an additional permanent magnet 525 or a plurality of additional permanent magnets 525 are furnished on the receiving housing 561 in order to generate a permanent magnetic field independently of a current source. Optionally, the magnetization of the permanent magnet 525 may be changed via corresponding magnetic pulses of the electric coil 8.

A channel 505 is furnished in the interior 563 between the receiving housing 561 and the shaft 562, and is partially filled with cylindrical rotating bodies 511, which are arranged in particular symmetrically around the circumference of the channel 505. The rotating bodies rotate against each other during the rotation of the two components 2, 3, because the rotating bodies 511 regularly contact the receiving housing 561 and/or the shaft 562 and thus roll with them.

To support the rolling and to ensure a rolling contact, at least one contact element 559 may be furnished in the form of a contact ring 559 (friction ring). A contact ring of this kind may be designed in particular as an O-ring (a round or square or rectangular ring) and for example may consist of a rubber-like material.

Such a contact ring 559 may be arranged, for example, in a circumferential groove 567 on the contact surface 565 of the receiving housing 561. It is also possible that an additional contact ring 559b is arranged in a groove 566 on the contact surface 564 on an enlarged circumferential ring 568 of the shaft 562.

It is possible and preferred that a contact ring 559 is arranged in the groove 567 and that a contact ring 559b is arranged in the inner circumferential groove 566 on the contact surface 564 of the circumferential ring 568.

Alternatively, it is also possible that the individual rotating bodies 511 are respectively provided with a contact ring 559c, and a contact ring 559c then extends around a rotating body 511. Even with such a configuration, it is ensured that the rotating bodies 511 and their contact ring 559 respectively have contact with the shaft 562 or the receiving housing 561, so that a continuous rotation is provided for the rotating body when the component 3 (or 2) is rotated.

Here in the exemplary embodiment, a defined axial distance between the receiving housing 561 and an axial surface of the circumferential ring 568 is ensured via a stop ring 583. The interior 563 is sealed off by a seal 546, so that the magnetorheological medium may not escape from the interior 563.

Between the cover or the holder at 582 and the receiving housing 561, a circumferential gap is furnished, on which a sensor 556 is arranged that serves as an angle sensor. Preferably, the angle sensor 556 consists of at least two parts 557 and 558, wherein the sensor part 557, for example, has magnets or other position markers or the like at specific angular positions, so a rotational movement of the component 3 is detectable via e.g. the sensor part 558 mounted on the electronics on the receiving housing 561. In this case, both an absolute angular position and a relative change in angle may be detected. With the angle sensor 556 or with a separate actuation sensor 554, an axial movement or axial force may be detected on the component 3 as a whole. For example, by exerting an axial force, a small change in distance between the holder 582 and the receiving housing 561 may be achieved, which may be detected by the actuation sensor 554. It is also possible that certain parts or the outer rotary ring of the component 3 are axially displaceable against a spring force, so that an axial actuation may be detected. The controller preferably operates at a control clock rate of 4 kHz or more.

It is possible that a cable feed 591 and a central channel are furnished to provide the required electrical power. However, it is preferred that an energy storage 528 is furnished, in particular internally. The energy storage 528 (battery or rechargeable battery) may also be furnished externally.

An axial distance 223 is furnished between the end face 570 on the shaft 562 and the end face 571 on the receiving housing 561. This axial distance is significantly less than the radial distance 574 between the circumferential ring 568 and the contact surface 565 in the receiving housing 561. A small distance is advantageous because the magnetic field 508 or the magnetic field lines pass through the gap 572 in the axial direction. In the case of a thin gap, relatively low magnetic losses are possible.

The functional principle for generating torques of the rotational damper according to FIG. 16 will be described below with reference to FIG. 17.

Figure 17:
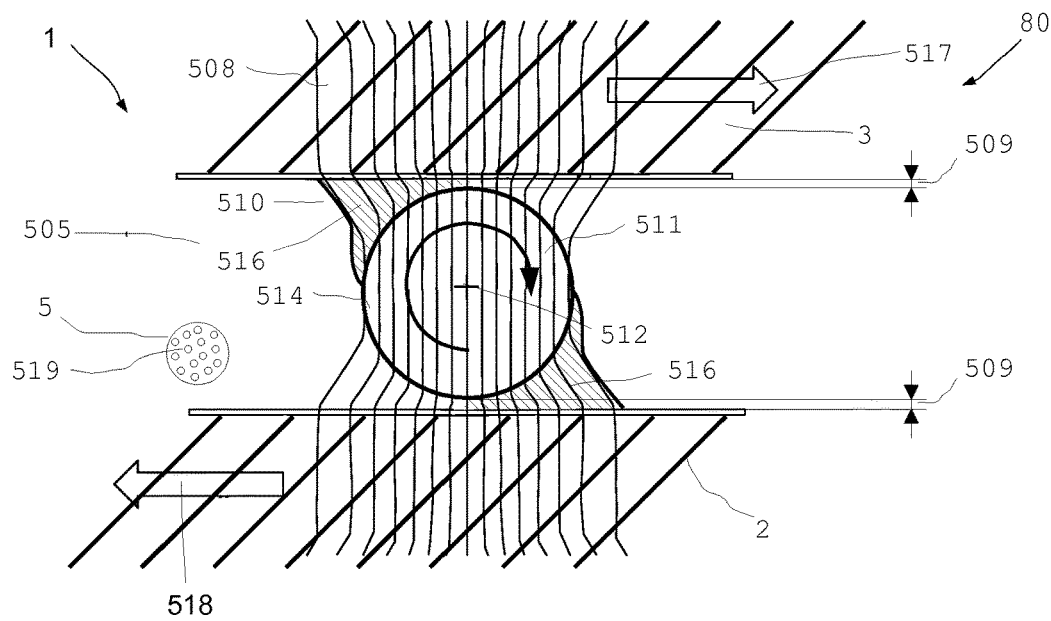
FIG. 17 a schematic sectional view of the damper of FIG. 16.

FIG. 17 shows a highly schematic cross-sectional view of a damper unit 80, which may be designed as a rotational damper 1 or as a linear damper. The damper unit 80 serves to influence the transmission of force between the two components 2 and 3. In this case, a rotating body 511 is furnished as a separate part between the two components 2 and 3 in FIG. 17 in any case. The components 2 and 3 may rotate relative to each other (see FIG. 16) or may be linearly displaceable. In any case, the rotating body 511 rotates during the relative movement. The rotating body 511 is formed here as a sphere 514. But it is also possible to form rotating bodies 511 as cylinders (FIG. 16) or ellipsoids, rollers or other rotatable rotating bodies. Non-rotationally symmetrical rotating bodies, such as, for example, a gearwheel or rotating body 511 with a specific surface structure, may also be used as rotating bodies. The rotating bodies 511 are not used for bearing against each other, but for transmitting torque.

Between the components 2 and 3 of the rotational damper 1, a channel 505 is furnished, which is filled in this case with a magnetorheological fluid 5, which for example comprises a carrier liquid as an oil, in which ferromagnetic particles 519 are present. Glycol, fat, and viscous substances may also be used as a carrier medium, without any limitation thereto. The carrier medium may also be gaseous or it may be dispensed with entirely (vacuum). In this case, the channel is filled only with particles that may be influenced by the magnetic field.

The ferromagnetic particles 519 are preferably carbonyl iron powder, with the particle size distribution depending on the specific application. A distribution particle size between one and ten micrometers is specifically preferred, but larger particles of twenty, thirty, forty and fifty microns are also possible. Depending on the application, the particle size may become significantly larger and even reach into the millimeter range (particle spheres). The particles may also have a special coating/jacket (titanium, ceramic, carbon, etc.), so that they may better withstand the high pressure loads that may arise depending on the application. The MR particles for this application may be manufactured not only from carbonyl iron powder (pure iron), but may e.g. also be made from specialized iron (harder steel).

The rotating body 511 is displaced by the relative movement 517 of the two components 2 and 3 in rotation about its rotational axis 512, and runs its course practically on the surface of the component 3. At the same time, the rotating body 511 runs on the surface of the other component 2, so that a relative speed 518 is present there.

In strict terms, the rotating body 511 has no direct contact with the surface of the component 2 and/or 3 and therefore does not roll directly on either one. The free distance 509 from the rotating body 511 to one of the surfaces of the component 2 or 3 is e.g. 140 pm. In a specific configuration with particle sizes between 1 pm and 10 pm, the free distance is in particular between 75 pm and 300 pm and particularly preferably between 100 pm and 200 pm.

The free distance 509 is in particular at least ten times a typical mean particle diameter. Preferably, the free distance 509 is at least ten times the diameter of a largest typical particle. The lack of direct contact results in a very low base friction/force/torque when the components 2 and 3 move relative to one another.

If the rotational damper 1 is subjected to a magnetic field, the field lines are formed based on the distance between the rotating bodies 511 and the components 2, 3. The rotating body consists of a ferromagnetic material and e.g. in this case consists of ST 37. The steel type ST 37 has a magnetic permeability pr of about 2000. The field lines pass through the rotating body and concentrate in the rotating body. At the radial inlet and outlet surface of the field lines on the rotating body, there is a high flux density in the channel 505. The non-homogeneous and strong field leads to a local and strong crosslinking of the magnetically polarizable particles 519. By the rotational movement of the rotating body 511 in the magnetorheological fluid toward the wedge that is being formed, the effect is greatly increased and the possible braking or coupling torque is extremely increased, far beyond the amount that is normally generated in the magnetorheological fluid. Preferably, the rotating body 511 and component 2, 3 are at least partially made of ferromagnetic material, and consequently the magnetic flux density becomes higher the smaller the distance between the rotating body 511 and components 2, 3. As a result, a substantially wedge-shaped area 516 forms in the medium, in which the gradient of the magnetic field strongly increases at the acute angle at the contact point/region of smallest distance.

Despite the distance between the rotating body 511 and components 2, 3, these may be offset from each other by the relative speed of the surfaces of the rotating bodies 511 in a rotary motion. Rotational movement is possible without, and also with, an acting magnetic field 508.

When the magnetorheological transmission apparatus 1 is exposed to a magnetic field 508 of a magnetic field generation system 7, which is not shown here in FIG. 17, the individual particles 519 of the magnetorheological fluid 5 are linked along the field lines of the magnetic field 508. It should be noted that the vectors drawn in FIG. 1 represent only roughly and schematically the area of the field lines that is relevant for influencing the MRF. The field lines enter the channel 505 substantially perpendicular to the surfaces of the ferromagnetic parts and, especially in the acute-angled area 510, they do not have to be rectilinear.

At the same time, some material from the magnetorheological fluid is also caused to rotate along the circumference of the rotating body 511, so that an acute-angled area 510 is formed between the component 3 and the rotating body 511. On the other side, a like acute-angled area 510 is formed between the rotating body 511 and the component 2. The acute-angled areas 510 may have a wedge shape 516, for example, in the case of cylindrically-shaped rotating bodies 511. By means of the wedge shape 516, the further rotation of the rotating body 511 is hindered, so that the effect of the magnetic field on the magnetorheological fluid is increased, because the magnetic field acting inside the acute-angled area 510 results in a stronger cohesion of the medium there. As a result, the effect of the magnetorheological fluid in the accumulation (the chain formation in the fluid and thus the cohesion or the viscosity) is enhanced, which makes further rotation or movement of the rotating body 511 more difficult.

As a result of the wedge shape 516, much larger forces or torques may be transmitted than would be possible with a comparable structure that only uses the shearing motion without a wedge effect.

The forces which may be transmitted directly by the applied magnetic field represent only a small part of the forces that may be transmitted by the apparatus. The wedge formation and thus the mechanical force amplification may be controlled by means of the magnetic field. The mechanical amplification of the magnetorheological effect may go so far that power transmission is possible even after switching off an applied magnetic field, when the particles were wedged.

It has been found that the wedge action of the acute-angled areas 510 achieves a significantly greater effect of a magnetic field 508 of a specific strength. In this case, the effect may be amplified many times over. In a specific case, an approximately ten times greater influence on the relative speed of two components 2 and 3 was observed in MRF couplings than in the prior art. The amplification that is possible depends on different factors. Optionally, the amplification may be reinforced by a greater surface roughness of the rotating body 511. It is also possible that outwardly projecting projections are furnished on the outer surface of the rotating body 511, which may lead to an even stronger wedge formation. The wedge effect is distributed over the surface of the rotating body 511 and the components 2 or 3.

Figure 18:
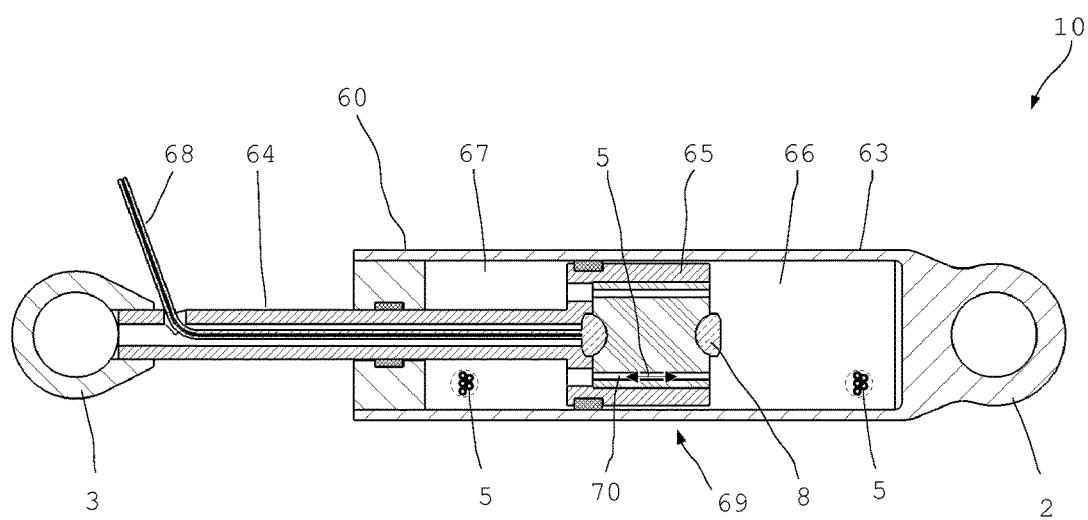
FIG. 18 a linear damper for e.g. the fitness equipment of FIG. 12.

FIG. 18 shows a linear damper 60 which is equipped with a valve device 69, which here comprises two damping channels 70. The linear damper 60, as a damping device 10, in this case has a first component 2 and a second component 3, which may be connected to two different housing parts, housings or bodies to dampen a relative movement in a fitness equipment. For a linear damping of this kind, e.g. the fitness equipment of FIG. 12 is suitable.

The linear damper 60 has a damper housing 63, in which a piston 65 is arranged. The piston 65 in this case is connected to a piston rod 64 which is fixedly connected to the second component 3.

The piston 65 divides the interior of the damper housing 63 into a first damper chamber 66 and a second damper chamber 67, which are at least partially filled with a magnetorheological medium and in particular with a magnetorheological fluid 5.

The piston 65 also serves as a valve device or comprises at least one such device. For this purpose, at least one flow channel or damping channel 70 is furnished in the piston 65. The flow of the magnetorheological fluid 5 is damped as it passes through the flow channel 70 of the piston 65. The flow direction is directed either from the first damper chamber 66 to the second damper chamber 67 or vice versa. Power may be supplied via a cable 68.

Figure 19:
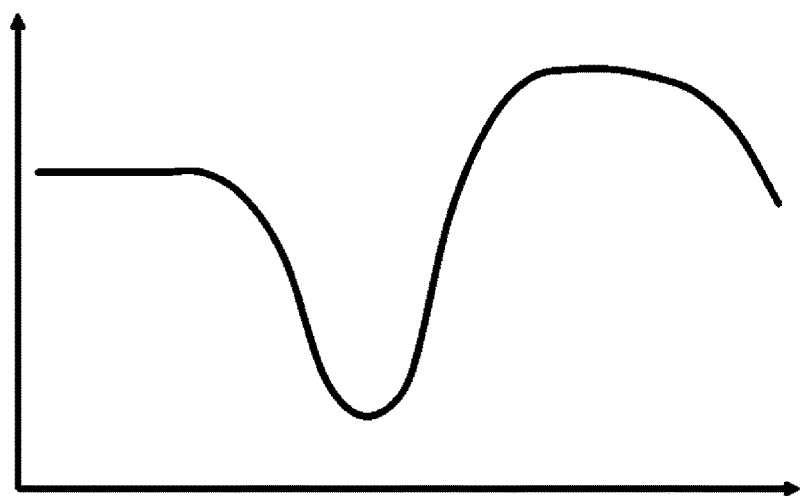
FIG. 19 a force progression.

FIG. 19 shows the force progression (on the foot) or the torque progression (on the device or in the knee joint) of training equipment via the angular position, e.g. in the leg press according to FIG. 14. The force is plotted on the Y-axis and the angle on the X-axis. Regarding joint and muscle load (body strain, long-term consequences . . . ), it may be disadvantageous, for example, in the case of this fitness equipment, when high forces are applied to the leg or foot at an angle of 90° between the upper and lower leg. At an angle of 50 to 80°, the forces may be higher, but should then be greatly reduced between 80° and 110°, and then again should be quite high when close to 180 degrees (leg extended). Immediately before complete extension (180°), it is again advantageous if the forces are lower.

Figure 19A:
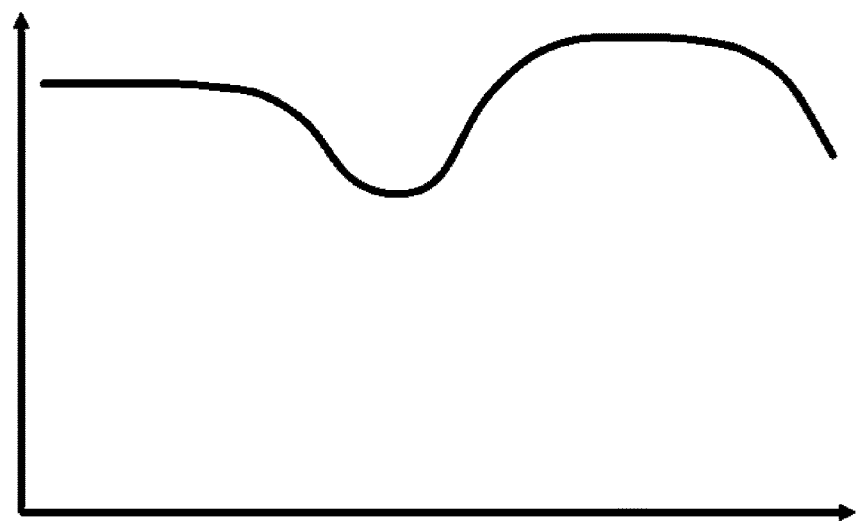
FIG. 19*a* another force progression.

FIG. 19a shows a force progression with smaller force differences than e.g. the progression of FIG. 19. The force is plotted on the y-axis and the angle is plotted on the x-axis. The torque or force progression may also be adapted to the user's condition on the day and/or the training period. This means that, for example, at the beginning of training lower forces/torques are applied to the training equipment, and these increase in the course of training, because the muscles/ the user have then been warmed up, and again decrease near the end of training, in the form of a "cooldown." Not only may the curve be scaled, but the progression may also be changed, so that the best possible training result is achieved with simultaneously low body strain.

Figure 20:
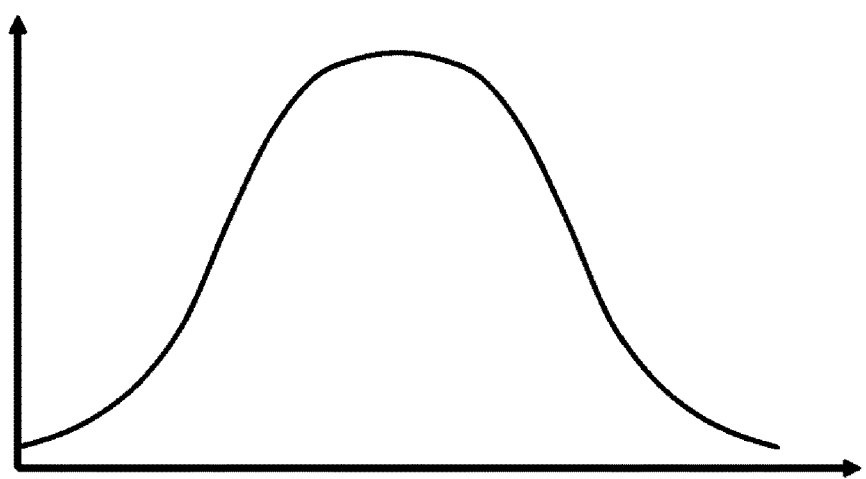
FIG. 20 another force progression.

FIG. 20 shows another force progression over the angle of movement. The force is plotted on the y-axis and the angle is plotted on the x-axis. This is advantageous in weightlifting or weight training because the elbow should not be stretched under load. This is achieved by means of lower force at the beginning of the movement (characteristic curve). The low force at the end of the movement results in a gentle end of the exercise, and by this means joint pain and possible muscle damage are prevented.

Figure 21:
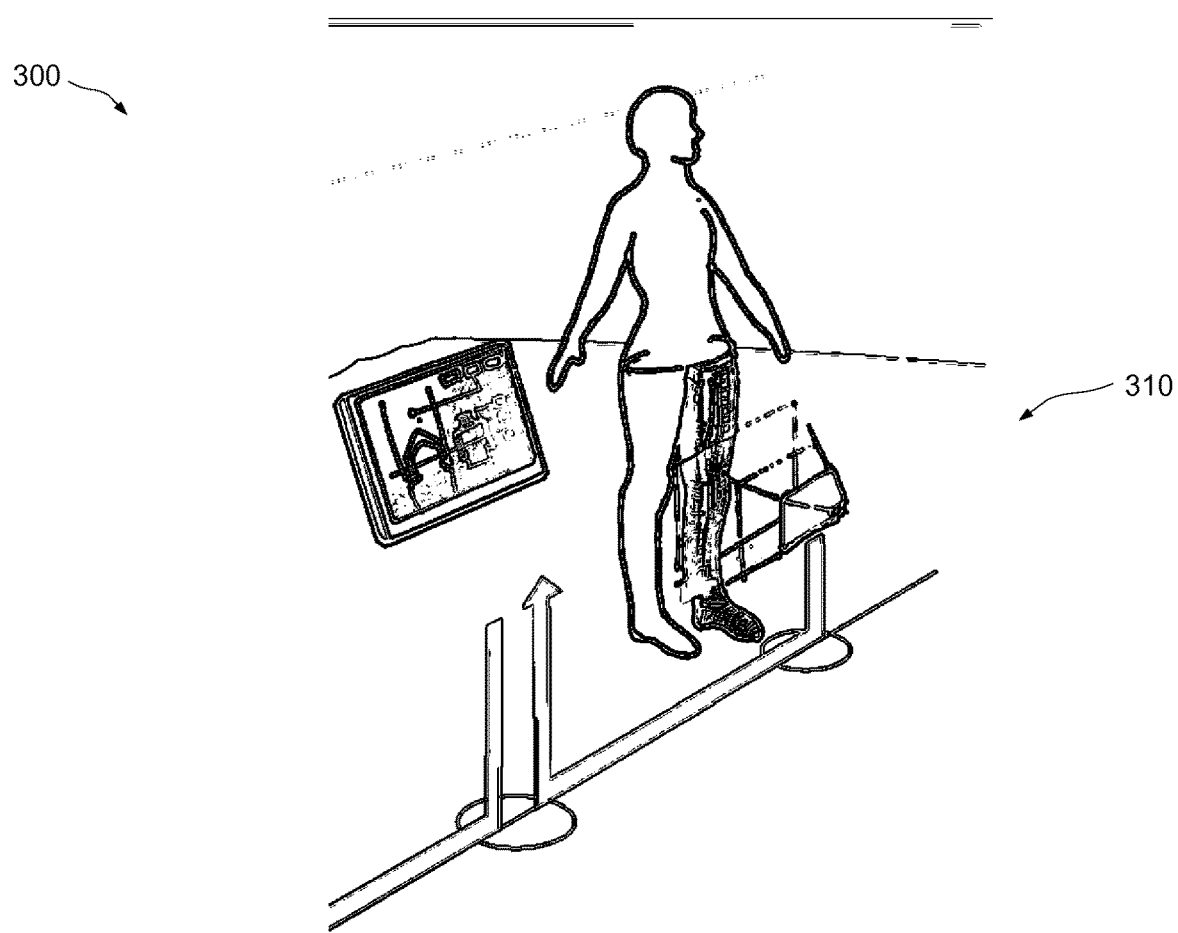
FIG. 21 a highly schematic training equipment with a near field detection system.

FIG. 21 shows a configuration with a near field detection system 310. In a possible variant, a customer comes e.g. to the fitness center and goes to a body scanner and/or analyzer. Here, the "leverage ratios" are determined and stored (e.g. upper arm, forearm, thighs, height . . . ). The customer receives a device (e.g. NFC wristband, chip, smart device such as a smartphone or watch or the like), which transmits this data to the fitness equipment 300 when using the device. In this way, the equipment is always optimally adjusted with respect to the training (e.g. force over path, torque over angle or the like) or tells the user how to adjust it (e.g. mechanically adjust the seat or the like) or adjusts the equipment on its own (e.g. by means of electric motors or the like).

Figure 22:
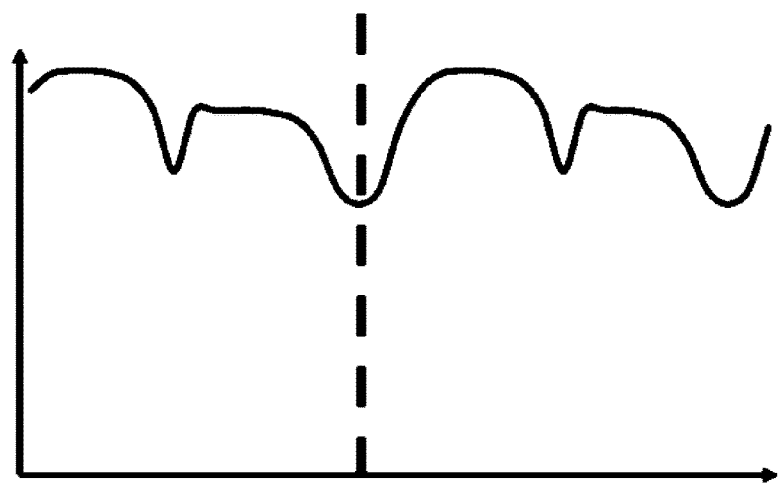
FIG. 22 another force progression.

FIG. 22 shows an exemplary force progression in the equipment 300 or ergotrainer according to FIG. 11. The force is plotted on the y-axis and the angle is plotted on the x-axis. The dashed line marks the division between the halves of the body. For example, to the right of the line, the damper adjustment is made for the right leg and to the left, it is made for the left leg. The damper settings are the same for both halves of the body in this case.

The curve starts in this case at 50°, the power increases and then proceeds in such a way as to protect the joints. In the lower pedal position (180°), the force is also reduced in the "almost" stretched leg in order not to transfer too a high load or stress the joints too much. After the low point (180°), the kick of the other leg begins. The angles change depending on the seat position (size, kinematics of the user . . . ), and the adaptive damper takes this connection into account.

Figure 23:
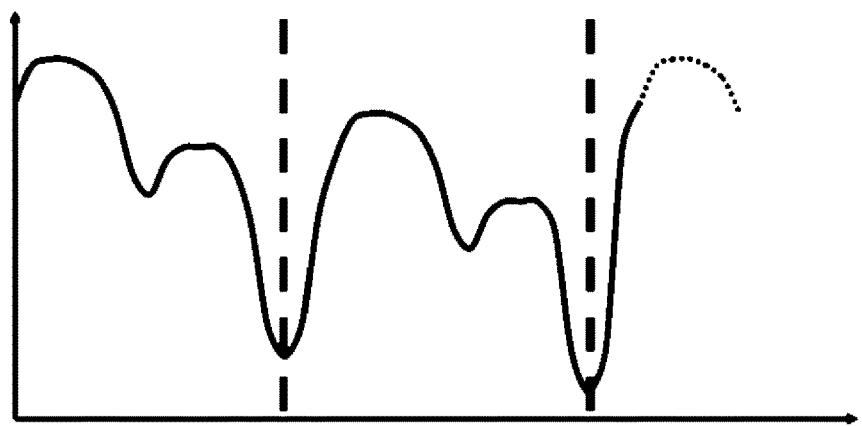
FIG. 23 yet another force progression.

FIG. 23 shows another exemplary force progression. The dashed lines mark the divisions between the halves of the body. The damper settings are different for both halves of the body. In this example, the left half of the body or the left leg has been weakened, e.g. by an accident or illness. The force progression is shown here over one movement cycle (360°) of an ergotrainer in the form of a bicycle. Here, the force progression (braking characteristic curve) of the left leg (left half of the body) is reduced, so that this half of the body is loaded less. Thus, for example, the rehabilitation process may be optimized after an accident. The muscle building may proceed in a more targeted way. But the reverse approach is also conceivable. An athlete wants to strengthen the now weaker body part, but still not overload the other part of the body, which the athlete may do in a targeted fashion by individually adjusting the braking force or torque damping.

The energy input is larger or smaller depending on the training equipment and training condition of the user. A necessary cooling to dissipate the energy is primarily possible in particular via the outer housing. In the rotational damper according to the invention, the MRF flows via feed lines and/or flow channels (e.g., FIGS. 7 and 8). Thus, an intermediate separate cooler may particularly useful to install here, so that the damper or the brake does not become too hot. Also possible is active cooling by means of additional pumping circuit, heat pipes (a heat pipe which allows a high heat flow density using heat of vaporization of a medium), or by means of an air stream (e.g. an electrical or mechanical cooling fan). This is advantageous for MRF actuators without a flow supply.

LIST OF REFERENCE SIGNS

| | |
|---|---|
| 1 | Rotational damper |
| 2 | Component |
| 3 | Component |
| 3a | Cover |
| 4 | Pivot shaft |
| 4a | Driver |
| 5 | Magnetorheological medium |
| 6 | Damping gap |
| 7 | Magnetic field generation system |
| 8 | Electric coil |
| 9 | Axis |
| 10 | Damping system |
| 11 | Seal device |
| 12 | internal component |
| 13 | Outer component |
| 14 | Connecting line |
| 15 | Reservoir |
| 16 | Axial length |
| 17 | Rotary encoder |
| 18 | Winding |
| 19 | End of 21, 22 |
| 20 | Spring device |
| 21 | Arm |
| 22 | Arm |
| 23 | Arm |
| 24 | Pole |
| 25 | Pole |
| 26 | Radial height of 6 |
| 27 | Diameter of 6 |
| 28 | Chamber |
| 29 | Separating element |
| 30 | Housing |
| 31 | End of 4 |
| 32 | End of 4 |
| 33 | Permanent magnet |
| 34 | Cover |
| 35 | Cavity, filling material |
| 36 | Field line |
| 37 | Bearing |
| 38 | Spacer sleeve |
| 60 | Linear damper |
| 63 | Housing |
| 64 | Piston rod |
| 65 | Piston |
| 66 | First damper chamber |
| 67 | Second damper chamber |
| 68 | Cable |
| 69 | Damping valve |
| 70 | Damping channel |
| 80 | Damper unit |
| 200 | Central controller |
| 201 | Computation unit |
| 202 | Current/torque regulator |
| 203 | System information |
| 204 | Actuator signal |
| 205 | Control voltage |
| 206 | Decentralized control |
| 300 | Training equipment |
| 301 | Actuating element |
| 302 | Control system |
| 303 | Transmission device |
| 304 | Frame |
| 305 | Seat |
| 310 | Near field detection system |
| 402 | Displacement device |
| 403 | Damper shaft |
| 404 | Displacement component |
| 405 | Displacement component |
| 407 | Control system |
| 408 | Field line |
| 411 | External toothing of 404 |
| 412 | Housing of 402 |
| 413 | Internal toothing of 405 |
| 414 | Rotational axis of 404 |

| | |
|---|---|
| 415 | Rotational axis of 405 |
| 417 | Damping channel |
| 420 | Ring in 412 |
| 421 | Guide unit |
| 422 | First end area |
| 423 | Central area |
| 424 | Second end area |
| 428 | Seal at 403 |
| 429 | Compensation volume |
| 432 | Angle sensor |
| 437 | Energy storage |
| 438 | Coil holder |
| 442 | Seal of 423 |
| 444 | Bearing |
| 505 | Channel |
| 508 | Field |
| 509 | Free distance |
| 510 | Acute-angled area |
| 511 | Rotating body |
| 512 | Rotational axis |
| 513 | Rotating body |
| 514 | Sphere |
| 515 | Cylinder |
| 516 | Wedge shape |
| 517 | Direction of relative movement |
| 518 | Direction of relative movement |
| 519 | Magnetic particles |
| 520 | Fluid |
| 525 | Permanent magnet |
| 527 | Control system |
| 528 | Energy storage |
| 530 | Bearing |
| 556 | Angle sensor |
| 557 | Sensor part |
| 558 | Sensor part, electronics |
| 559 | Contact ring, friction ring |
| 560 | Baseplate |
| 561 | Receiving housing |
| 562 | Shaft |
| 564 | Contact surface of 562 |
| 565 | Contact surface of 561 |
| 566 | Groove |
| 567 | Groove |
| 568 | Circumferential ring with 564 and |
| 569 | Receiving space for 8 |
| 570 | End face of 568 |
| 571 | End face of 561 |
| 572 | Gap |
| 580 | Cover |
| 581 | Screw |
| 582 | Holder |
| 583 | Stop ring |
| 591 | Cable |

The invention claimed is:

1. Training equipment for targeted muscle actuation, the training equipment comprising:
at least one at least partially muscle-powered actuating element to be moved by a user of the training equipment during a training exercise;
a damping system having at least two components that are movable relative to one another, one of said components being operatively connected with said actuating element and configured to damp a movement of said actuating element, said damping system having a field-sensitive rheological medium and a field generation system for generating and controlling a field strength, and for influencing a damping of said actuating element; and
a control system configured to targetedly control said field generation system based on at least one training parameter, and configured to damp a movement of said actuating element based on the training parameter;
said control system having a near field detection system with a near field sensor to detect a body posture and a movement of the user during the training exercise for targetedly controlling the movement of said actuating element and said field generation system based on the body posture and the movement of the user;
said control system being configured to adapt the training parameter in dependence on the body posture and the movement of the user detected by said near field detection system, and said damping system being configured for variably adjusting the damping of said actuating element in real time, and for providing feedback to the user by selectively damping the movement of the actuating element in real time based on the current body posture and the movement of the user detected by said near field detection system.

2. The training equipment according to claim 1, wherein said control system is configured to adjust a damping force to be applied in order to move one of said two components based on the training parameter.

3. The training equipment according to claim 1, wherein said control system is configured to set, based on the training parameter and in real time during an exercise by the user, a path and/or angle of rotation over which at least one of said two components is movable.

4. The training equipment according to claim 1, wherein said control system is configured to vary the damping during at least a single actuation of said actuating element.

5. The training equipment according to claim 1, wherein the training parameter is selected from the group consisting of force, speed, acceleration, distance, direction of movement, a movement path and an angle that are furnished for actuating said actuating element.

6. The training equipment according to claim 1, wherein said control system is configured to control said field generation system based on the at least one training parameter in dependence on at least one other training parameter.

7. The training equipment according to claim 1, wherein said control system is configured to vary the damping during a single actuation of said actuating element adaptively based on the body posture and the movement of the user.

8. The training equipment according to claim 1, wherein said damping system is configured to change the damping by at least 30% in less than 100 milliseconds.

9. The training equipment according to claim 1, wherein said damping system is configured to block an at least partially muscle-powered movement of said actuating element, by means of said field generation system and said field-sensitive rheological medium.

10. The training equipment according to claim 1, wherein said actuating element is selected from the group consisting of a pedal drive, a leg lever, a knee lever, an arm lever, a back lever, a belly lever, a trunk lever, a cable, and an oar lever.

11. The training equipment according to claim 1, wherein:
said damping system includes at least one rotational damper; and
one of said components is an inner component and another of said components is an outer component, said outer component at least partially surrounds said inner component radially, wherein a ring-shaped damping gap is disposed between said components, bounded radially inwardly by said inner component and radially outwardly by said outer component and at least partially filled with said field-sensitive rheological medium, and wherein said field generating system is configured to expose said damping gap to a magnetic field, in order to damp a pivoting movement between said components being two mutually pivotable components about an axis.

12. The training equipment according to claim 11, further comprising at least one transmission device configured to at least partially convert a linear movement of said actuating element into a pivoting movement of one of said two components, to thereby damp the linear movement by way of a rotational damper.

13. The training equipment according to claim 1, further comprising a plurality of at least partially radially extending arms being furnished on at least one of said components and at least a part of said partially radially extending arms is equipped with an electrical coil with at least one winding, wherein said winding respectively extends adjacent to an axis of said components and spaced away from the axis.

14. The training equipment according to claim 1, wherein said damping system has at least one rotational damper with at least one displacement device, said displacement device has a damper shaft and intermeshing displacement components, and said damping system is configured to damp a rotational movement of said damper shaft.

15. The training equipment according to claim 14,
wherein said field-sensitive rheological medium is a field-sensitive magnetorheological fluid being a working fluid for an operation of said displacement device; and
wherein said field generation system has at least one electrical coil being a magnetic field source generating a magnetic field and and being controlled by means of said associated control system, and said field-sensitive magnetorheological fluid is influenced by means of the magnetic field, in order to adjust a damping of a rotational movement of said damper shaft.

16. The training equipment according to claim 1, wherein:
said damping system has at least one controllable damping valve and at least one linear damper with at least one first damper chamber and at least one second damper chamber, which are coupled together via said at least one controllable damping valve, said controllable damping valve having at least one damping channel formed therein; and
said field generation system is associated with said damping valve and serves to generate and control a field strength in said at least one damping channel of said damping valve, wherein said field-sensitive rheological medium is furnished in said damping channel.

17. The training equipment according to claim 16, wherein said linear damper has a damper chamber filled with said field-sensitive rheological medium and a piston disposed to move relative to said damper chamber.

18. The training equipment according to claim 1, wherein said damping system is configured to enable a damping characteristic for a left half of the training equipment to be set, at least partially, to a different damping characteristic than for a right half of the training equipment.

19. The training equipment according to claim 1, wherein the damping furnished for a particular half of the training equipment is at least partially variable during a single actuation of said actuating element.

20. The training equipment according to claim 1, wherein the damping is at least partially variable based on at least one signal of a near field detection system.

21. The training equipment according to claim 1, wherein said near field sensor includes an image sensor and said control system is configured to control said damping system in response to image information concerning a user of the training equipment in real time.

22. A method for operating training equipment for targeted muscle actuation, which comprises the steps of:
actuating an at least partially muscle-powered actuating element by a user during a training exercise;
providing a damping system having at least two components that are movable relative to one another, wherein at least one of the components is operatively connected with the actuating element, and a movement of the actuating element is damped with the damping system which has a field-sensitive rheological medium and at least one field generation system to generate and control a field strength,
influencing at least one damping characteristic by the field generation system and controlling the field generation system based on at least one training parameter by a control system, and thereby damping a movement of the actuating element, taking into account the training parameter,
providing the control system with at least one sensor configured to detect a body posture and a movement of the user of the user during the training exercise for targetedly controlling the movement of the actuating element and the field generation system based on the body posture and the movement of the user; and
adapting the training parameter in real time with the control system in dependence on the body posture and the movement of the user detected by the at least one sensor, and providing feedback to the user by selectively and variably adjusting a damping of the actuating element in real time, based on the body posture and the movement of the user detected by the at least one sensor.

23. The method according to claim 22, which further comprises:
monitoring at least one of a body posture or a movement of the user for at least a single actuation of the actuating element; and
adjusting the damping in a targeted fashion, taking into account the body posture or the movement of the user, and thereby setting an optimal force/torque curve with regard to a desired training result.

24. The method according to claim 23, which further comprises adjusting the damping more than once, during a single actuation of the actuating element, based on the body posture or the movement of the user.

25. The method according to claim 23, wherein less than 100 ms elapse between an actuation of the actuating element, for which the body posture or the movement of the user is monitored, and a resulting adjustment of the damping.

26. The method according to claim 22, which further comprises determining at least one characteristic value for a movement of the first and second components relative to each other repeatedly in real time and generating with the field generation system a field only when there is a relative movement of the first and second components relative to one another and deriving a field strength to be set in real time using the characteristic value and the field strength to be set in real time by means of the field generation system in order to set in real time a damping which results from the determined characteristic value.

27. The method according to claim 22, which comprises providing at least one sensor for recording image information and controlling the damping system in response to the image information concerning a user of the training equipment in real time.

28. A method for operating training equipment for targeted muscle actuation, which comprises the steps of:
- actuating an at least partially muscle-powered actuating element by a user during a training exercise;
- detecting a body posture of the user during the training exercise and a speed at which the training exercise is being performed;
- providing a damping system having at least two components that are movable relative to one another, wherein at least one of the components is operatively connected with the actuating element, and a movement of the actuating element is damped with the damping system which has a field-sensitive rheological medium and at least one field generation system to generate and control a field strength,
- influencing at least one damping characteristic by the field generation system and controlling the field generation system based on the body posture and the speed by a control system, and thereby damping a movement of the actuating element, taking into account the body posture and the speed with which the exercise is being performed,
- controlling the field generation system with the control system during the training exercise for selectively and variably adjusting a damping of the actuating element in real time and, in addition, providing haptic feedback to the user as a function of the body posture and the speed with which the training exercise is being performed.

29. The training equipment according to claim 28, wherein the haptic feedback to the user is a haptic chatter or jerking.

* * * * *